United States Patent
Britz-McKibbin

(10) Patent No.: US 10,234,421 B2
(45) Date of Patent: Mar. 19, 2019

(54) METHODS FOR IODIDE DETERMINATION

(71) Applicant: McMaster University, Hamilton (CA)

(72) Inventor: Philip Britz-McKibbin, Hamilton (CA)

(73) Assignee: McMaster University, Hamilton (CA)

( * ) Notice: Subject to any disclaimer, the term of this patent is extended or adjusted under 35 U.S.C. 154(b) by 0 days.

(21) Appl. No.: 15/281,205

(22) Filed: Sep. 30, 2016

(65) Prior Publication Data
US 2017/0146486 A1 May 25, 2017

Related U.S. Application Data

(60) Provisional application No. 62/234,801, filed on Sep. 30, 2015.

(51) Int. Cl.
| | |
|---|---|
| *G01N 27/447* | (2006.01) |
| *G01N 33/02* | (2006.01) |
| *G01N 33/14* | (2006.01) |
| *G01N 33/18* | (2006.01) |
| *G01N 33/48* | (2006.01) |
| *G01N 33/483* | (2006.01) |
| *G01N 33/49* | (2006.01) |
| *G01N 33/50* | (2006.01) |
| *G01N 33/487* | (2006.01) |
| *G01N 33/493* | (2006.01) |

(52) U.S. Cl.
CPC . *G01N 27/44773* (2013.01); *G01N 27/44747* (2013.01); *G01N 33/48707* (2013.01); *G01N 33/49* (2013.01); *G01N 33/493* (2013.01); *G01N 27/44721* (2013.01)

(58) Field of Classification Search
CPC ........ G01N 31/00; G01N 33/00; G01N 33/02; G01N 33/14; G01N 33/18; G01N 33/48; G01N 33/483; G01N 33/487; G01N 33/49; G01N 33/491; G01N 33/492; G01N 33/493; G01N 33/50; G01N 27/00; G01N 27/26; G01N 27/447; G01N 27/44773

See application file for complete search history.

(56) References Cited

U.S. PATENT DOCUMENTS

2008/0107851 A1* 5/2008 Nasu .................. B01F 13/0818
428/35.8

OTHER PUBLICATIONS

Macedo et al. "A Robust method for Iodine Status Determination in Epidermiological Studies by Capillary Electrophoresis"); Anal. Chem. 2014, 86, 10010-10015 (Year: 2014).*

Hirokawa, T., et al., "High-sensitivity capillary electrophoresis determination of inorganic anions in serum and urine using on-line preconcentration by transient isotachophoresis." J. Chromatogr. B 2004, 811, 165-170.

(Continued)

*Primary Examiner* — Susan D Leong
(74) *Attorney, Agent, or Firm* — Bereskin & Parr LLP/S.E.N.C.R.L., S.R.L.; Patricia Folkins

(57) ABSTRACT

The present application is directed to the use of electrophoresis with UV detection in the determination of iodine nutritional status in human biological specimens, specifically for monitoring iodine deficiency/inadequacy in large-scale epidemiological studies. In particular, the present application is directed to a method for determining iodide and iodide uptake inhibitors in a human biological sample when using sample self-stacking with capillary electrophoresis and UV detection.

20 Claims, 16 Drawing Sheets

(56) References Cited

OTHER PUBLICATIONS

Xu, Z., et al.,"Sensitive determination of anions in saliva using capillary electrophoresis after transient isotachophoretic preconcentration." Talanta 2008, 77, 278-281.

Nori De Macedo, A. et al., A., et al., Urinary Iodide Status Determination by Capillary Electrophoresis: A Population Health Perspective, 97th Canadian Chemistry Conference and Exhibition, Vancouver, B.C. Jun. 1-4, 2014.

Timerbaev, Andrei R., et al., "Analysis of highly saline samples by capillary zone electrophoresis: enhanced direct UV detection of inorganic anions using on-capillary preconcentration and clean-up techniques", Journal of Chromatography A, 888, 2000, 309-319.

Pantuckova, Pavla, et al., "Fast and simple method for determination of iodide in human urine, serum, sea water, and cooking salt by capillary zone electrophoresis", Electrophoresis 2004, 25, 1102-1111.

Huang, Zhou et al., "Speciation studies by capillary electrophoresis—simultaneous determination of iodide and iodate in seawater", Anal Bioanal Chem 2004, 378, 1836-184t.

* cited by examiner

METHODS FOR IODIDE DETERMINATION

CROSS REFERENCE TO RELATED APPLICATIONS

The present application claims the benefit of priority from U.S. provisional patent application No. 62/234,801 filed on Sep. 30, 2015, the contents of which are incorporated herein by reference.

FIELD

The present application is directed to a method for determining iodide content in a sample using electrophoresis performed for example, in a capillary, microchip or related device.

BACKGROUND

Iodine is an essential micronutrient needed for the biosynthesis of thyroid hormones, which are critical in the regulation of cellular metabolism, as well as in normal growth and mental development.[1,2] In order to provide a consistent source of iodine to the population and prevent iodine deficiency disorders (IDDs), many countries have adopted table salt iodization as a public health policy. Although significant improvement has been achieved in the reduction of endemic goiter and cretism, other IDDs remain problematic with almost 2 billion people worldwide at risk for iodine insufficiency[3] that is associated with impaired cognitive development in children, as well as weight gain, depression, thyroid disorders and cardiovascular diseases later in life.[4-7] Several developed countries in which iodine deficiency was believed to be eradicated some decades ago, are facing mild iodine deficiency due to reduced intake of iodine-rich foods, increased consumption of non-iodized processed foods and/or exposure to iodide uptake inhibitors in the environment.[8-11] For instance, about one third of pregnant women in the United States are marginally iodine deficient.[5] Therefore, continuous monitoring of iodine status through iodide detection is an essential part of universal salt iodization programs[10,12,13] with dietary iodide intake recommended to be 150 μg/day for adults and 250 μg/day for pregnant women.[3] The best single measurement to evaluate median iodine intake in the population is via excreted urinary iodide, which represents more than 90% of the iodine recently ingested.[2,3,14,15] For this reason, iodide concentrations from random spot urine samples are often used in epidemiological studies for iodine status assessment. However, simple, selective and cost-effective assays are needed to analyze sub-micromolar levels of urinary iodide for population health.[16]

A kinetic spectrophotometric assay based on the classic Sandell-Kolthoff reaction is the most widely used method for urinary iodine determination, where iodide serves as a catalyst for the reduction of the yellow Ce(IV) to colorless Ce(III) in the presence of As(III).[16,17] Although the assay is well established, a number of different protocols exist that are time-consuming, involve handling of toxic reagents, and require specially designed sealing cassettes for acid digestion in microplates to remove interferences in urine. Inductively coupled plasma-mass spectrometry (ICP-MS) is also used for urinary iodine determination. A simple dilution step with addition of an isotopic internal standard is used to minimize matrix effects while achieving low detection limits.[17,18] However, the method is not specific for iodide, measuring instead total iodine in the sample, thus it is prone to bias due to iodine-containing compounds not completely bioavailable for thyroid uptake, such as iodinated drugs (e.g., amiodarone), radiologic contrast agents (e.g., iopamidol), and food additives (e.g., erythrosine). Also, large sample volumes (>200 μL) are often required for sample preparation when using pneumatic nebulizers with ICP-MS that limit the use of stored urine specimens in bio-repositories with finite volumes. Ion-exchange chromatography coupled to ICP-MS has been introduced for improved speciation of iodine, including iodide, iodate and iodine-containing analogues of tyrosine from edible seaweed.[19] However, ICP-MS and other MS-based methods[17,18] demand more costly infrastructure and operating costs that are not suitable for developing countries. Alternatively, capillary electrophoresis (CE) with UV detection has been reported for the analysis of iodide in urine[20,21] and other complex sample matrices.[21-25] Wide-bore capillaries[21] and/or transient isotachophoretic (tITP) preconcentration[20,22-24] are needed to attain sub-micromolar detection limits for assessment of iodine nutritional insufficiency (<0.79 μM or <100 μg/L) by the World Health Organization.[3] However, the lack of rigorous method validation and long-term robustness studies has prevented the translation of CE-based assays for large-scale epidemiological or clinical studies.[26]

SUMMARY

In the present application capillary electrophoresis with UV detection was used in the determination of iodide content in samples, such as human biological specimens. Such methods are useful, for example, for monitoring of iodine deficiency/insufficiency in large-scale epidemiological studies in support of universal iodization programs worldwide. The same assay can also be used to simultaneously measure environmental iodide uptake inhibitors, including but not limited to, thiocyanate, bromide and nitrate. Selectivity is achieved by using, for example, an acidic background electrolyte in conjunction with dynamic complexation via α-cyclodextrin (α-CD), which also allows for sample self-stacking to boost concentration sensitivity via on-line sample pre-concentration when using UV absorbance detection in order to achieve low sub-micromolar detection limits.

Accordingly, the present application includes a method for determining iodide content in a sample comprising:
(a) subjecting the sample to sample self-stacking by transient isotachophoresis with subsequent zonal electrophoretic separation in which a background electrolyte (BGE) comprising an effective amount of a hydroxide salt, an effective amount of a complexing agent and an effective amount of an inorganic acid is used to generate an electropherogram; and
(b) determining the content of iodide in the sample from the electropherogram,
wherein the BGE has a pH in the range of about 2 to about 4.

The present application also includes a method for monitoring the iodine nutritional status of a population by measuring iodide and, optionally, iodide uptake inhibitors in a sample from a representative number of subjects from the population using a method as defined in the application.

The present application also includes a background electrolyte (BGE) composition for sample self-stacking based on transient isotachophoresis comprising an effective amount of a hydroxide salt, an effective amount of a complexing agent and an effective amount of an inorganic acid.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

BRIEF DESCRIPTION OF THE DRAWINGS

The embodiments of the application will now be described in greater detail with reference to the attached drawings in which.

DETAILED DESCRIPTION

I. Definitions

Figure 1:
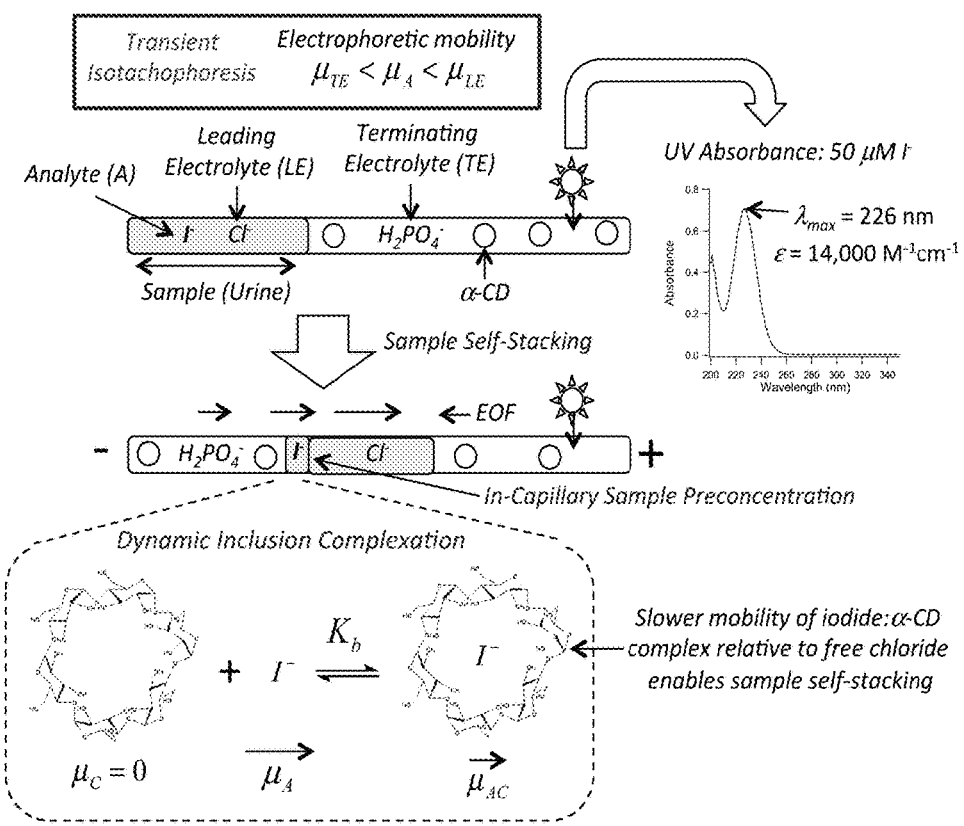
FIG. 1 shows a schematic describing the injection configuration and buffer conditions for the detection of urinary iodide by CE and UV detection, using on-line sample self-stacking in one embodiment of the application.

Unless otherwise indicated, the definitions and embodiments described in this and other sections are intended to be applicable to all embodiments and aspects of the present application herein described for which they are suitable as would be understood by a person skilled in the art.

Unless otherwise indicated, the definitions and embodiments described in this and other sections are intended to be applicable to all embodiments and aspects of the present application herein described for which they are suitable as would be understood by a person skilled in the art.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this application and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "an acid" should be understood to present certain aspects with one acid or two or more additional acids.

The term "and/or" as used herein means that the listed items are present, or used, individually or in combination. In effect, this term means that "at least one of" or "one or more" of the listed items is used or present.

The term "electrophoresis" refers to a family of electrokinetic separation methods performed in submillimeter diameter capillaries, in micro- and nanofluidic channels, in microchips or in related devices. The method comprises the migration of analytes through electrolyte solutions under the influence of an electric field. Analytes may be concentrated or "focused" by means of gradients in conductivity and pH. When the method is performed in a capillary or in micro- and nanofluidic channels is generally referred to as "capillary electrophoresis" or "CE".

The terms "isotachophoresis" or "ITP" refer to an analytical technique for selective separation and concentration of ionic analytes, specifically, a form of CE in which charged analytes are separated based on ionic mobility. Conventional ITP separations comprise the sample being introduced between a zone of leading electrolyte (LE) and a zone of a terminating electrolyte (TE). The LE is defined by having a higher ionic mobility, while TE has a lower ionic mobility. The LE and TE are selected such that the analytes of interest have intermediate ionic mobility, thus focusing the analytes at the LE/TE interface.

The term "tITP" refers to transient ITP. The technique is accomplished by dissolving the analyte sample in the TE and sandwiching the sample/TE plug between LE zones or vice versa: a sample/LE plug can be also sandwiched between TE zones. Sample self-stacking is a form of tITP when a LE (e.g., chloride) is naturally present in a sample (e.g., urine), whereas only a TE is introduced in the BGE (e.g., phosphate, pH 2) for on-line preconcentration of low levels of iodide.

The term "ionic strength" refers to a quantity of measure representing the strength of the electric field in a solution, equal to the sum of the molarities of each type of ion present multiplied by the square of their charges.

The term "inorganic acid" refers to an acid that does not contain carbon and is composed of an acidic hydrogen bonded to one or more electronegative atoms, including but not limited to, oxygen, chlorine, bromine and fluorine.

The term "electropherogram" refers to a plot of results from the separation of components from a mixture produced by electrophoresis.

The terms "BGE" or "background electrolyte" refers to an electrolyte solution containing ions that conduct electricity under an applied external voltage, which also serve to control solution pH (i.e., act as a buffer). The BGE can also include other additives in the solution that modify the effective mobility of iodide (and other anions) as required for sample self-stacking (i.e., on-line sample preconcentration) and electrophoretic separation (i.e., resolution), such as α-CD.

II. Methods of the Application

The present application discloses a new sample self-stacking CE assay to analyze sub-micromolar levels of urinary iodide, optionally with simultaneous determination of iodide uptake inhibitors.

Accordingly, the present application includes a method for determining iodide content in a sample comprising:
(a) subjecting the sample to sample self-stacking by transient isotachophoresis with subsequent zonal electrophoretic separation in which a background electrolyte (BGE) comprising an effective amount of a hydroxide salt, an effective amount of a complexing agent and an effective amount of an inorganic acid is used to generate an electropherogram; and
(b) determining the content of iodide in the sample from the electropherogram,
wherein the BGE has a pH in the range of about 2 to about 4.

Transient isotachophoresis (tITP) is known in the art to be easily implemented in electrophoresis separations as a pre-concentration step, making the detection method more sensitive (i.e., UV absorbance). Thus, on-line sample pre-concentration was performed by sample self-stacking as a pre-treatment step prior to zonal electrophoretic separation and on-line optical detection. In some embodiments, the electrophoresis is capillary electrophoresis (CE).

In some embodiments, the concentration of iodide in the sample solution is adjusted, for example by dilution or concentration, so that it is in the range of about 0.2 µM to about 4 µM solution. In some embodiments, the sample is diluted with deionized water by about 1.5-fold to about 4-fold. In some embodiments, the sample is diluted by about 1.5-fold to about 2-fold. A person skilled in the art can readily determine whether or not a sample requires dilution or concentration by performing the methods of the application on an undiluted or unconcentrated sample and if the concentration of iodide in the sample is too high for suitable detection by electrophoresis, diluting the sample, and if the concentration of iodide in the sample is too low for suitable detection by electrophoresis, concentrating the sample.

In some embodiments, an internal standard is added to the sample prior subjecting to ITP. In some embodiments, the internal standard is naphthalene disulfonic acid (NDS).

The sample is from any source that one wishes to test for iodide content, including, but not limited to bodily fluids, environmental samples, food and drink samples. In some embodiments, the sample is a biological sample. In some embodiments, the biological sample is selected from urine, blood (e.g. serum and plasma) and sweat. In some embodiments the biological sample is from a human or animal. In some embodiments, the sample is from the environment. In some embodiments the same is from a food, drinking water, or soil. In some embodiments, the biological sample is human urine. In some embodiments, the biological sample is human sweat. In some embodiments the sample is treated, for example by drying, extraction, purification, dilution and/or concentration prior to performing the method of the application. In some embodiments the sample has been collected and dried onto a substrate, such as filter paper. In some embodiments, the sample is a urine or blood sample that has been collected on filter paper, for example from urine spot analyses.

In some embodiments, the effective amount of the complexation agent is from about 30 mM to about 60 mM. In some embodiments, the effective amount of the complexation agent is from about 30 mM to about 50 mM. In some embodiments, the effective amount of the complexation agent is about 46 mM. In some embodiments, the effective amount of the complexation is about 44 mM. In some embodiments, the effective amount of the complexation agent is about 36 mM. In some embodiments, the complexation agent is selected from starch/iodine, various ionophores for iodide, and α-cyclodextrin. In some embodiments, the complexation agent is α-cyclodextrin.

One factor for separation optimization within the method of the present application is the ionic strength of the BGE/TE. In some embodiments, a high ionic strength BGE/TE ensures good sample self-stacking performance for trace levels of iodide. The high ionic strength is provided by the hydroxide salt and inorganic acid composite present in the BGE.

In some embodiments, the effective amount of the hydroxide salt is from about 150 mM to about 200 mM. In some embodiments, the effective amount of the hydroxide salt is from about 160 mM to about 190 mM. In some embodiments, the effective amount of the hydroxide salt is about 180 mM. In some embodiments, the hydroxide salt is selected from sodium hydroxide, potassium hydroxide and lithium hydroxide. In some embodiments, the hydroxide salt is lithium hydroxide.

In some embodiments, the effective amount of the inorganic acid is from about 150 mM to about 200 mM. In some embodiments, the effective amount of the inorganic acid is from about 160 mM to about 190 mM. In some embodiments, the effective amount of the inorganic acid is about 180 mM. In some embodiments, the inorganic acid is phosphoric acid.

In some embodiments, BGE has a pH of 3. The low pH is provided by the acidic buffer (i.e. inorganic acid) which is used to suppress electroosmotic flow (EOF) while ensuring the inorganic acid exists as the predominant species in solution since it also functions as a LE during sample self-stacking.

Proceeding the dilution step (for example for urine), the sample is subjected to sample self stacking and zonal electrophoresis using techniques, such as capillary electrophoresis, under optimal separation conditions. In some embodiments, the optimal separation conditions comprise
 a) a hydrodynamic injection time of about 60 s to about 100 s at about 20° C. to about 40° C., or at about 25° C.; and
 b) a reversed polarity using an applied voltage of about −10 kV to about −30 kV, or about −25 kV.

In some embodiments, the hydrodynamic injection time is about 70 s to about 90 s. In some embodiments, the hydrodynamic injection time is about 80 s.

In some embodiments, the applied voltage is about −15 kV to about −20 kV. In some embodiments, the applied voltage is about −18 kV.

In some embodiments, the iodide content of the sample is determined by using isotachophoretic capillary electrophoresis with UV detection.

In some embodiments, the quantity of iodide in the sample is determined by measuring light absorbance at a wavelength at which the iodide significantly absorbs light. In some embodiments, the wavelength at which the light absorbance is measured is 226 nm.

In some embodiments, the determining the content of iodide in the sample from the electropherogram is performed by calculating the relative peak area (RPA) for the peak in the electropherogram corresponding to iodide. In some embodiments, the RPA for the iodide peak for the sample is compared to a standard calibration curve to determine the amount of iodide in the sample, In some embodiments, the method further comprises determining one or more iodide uptake inhibitor content in the sample wherein, in (b) the content of one or more iodide uptake inhibitors in the sample is also determined from the electropherogram.

In some embodiments, the iodide uptake inhibitor is selected from nitrate, bromide and/or thiocyanate. In some embodiments, the iodide uptake inhibitor is nitrate. In some embodiments, the iodide uptake inhibitor is bromide. In some embodiments, the iodide uptake inhibitor is thiocyanate.

In some embodiments, the iodide uptake inhibitor content of the sample is determined by using sample self-stacking with capillary electrophoresis and UV detection.

In some embodiments, the quantity of iodide uptake inhibitor in the sample is determined by measuring light absorbance at a wavelength at which the iodide uptake inhibitor significantly absorbs light. In some embodiments, the wavelength at which the light absorbance is measured is in the range of about 214 nm.

In some embodiments, the determining the content of one or more iodide uptake inhibitors in the sample from the electropherogram is performed by calculating the relative peak area (RPA) for the peak(s) in the electropherogram corresponding to the one or more iodide uptake inhibitors. In some embodiments, the RPA for the one or more iodide uptake inhibitors peak(s) for the sample is compared to a standard calibration curve to determine the amount of one or more iodide uptake inhibitors in the sample, The present application also includes a method for determining iodide and one or more iodide uptake inhibitor content in a sample, the method comprising:
 a) diluting the sample by about 1.5-fold to about 4-fold;
 b) subjecting the diluted sample to sample self-stacking via transient isotachophoresis followed by zonal electrophoretic separation by capillary electrophoresis utilizing a background electrolyte (BGE), the background electrolyte comprising:
  (i) an effective amount of hydroxide salt;
  (ii) an effective amount of a complexing agent; and
  (iii) an amount of an inorganic acid to provide a pH in the range of about 2 to about 4; and
 c) determining the quantity of iodide and one or more iodide uptake inhibitors in the sample from the electropherogram.

The present application further includes a method for monitoring iodine deficiency in a population by determining iodide content in a sample from a representative number of subjects from the population using a method as defined in the application. Accordingly the methods of the application can be used to assess the nutritional iodine status of a population (epidemiological screening). A person skilled in the art would know how to determine the representative number of subjects required to obtain statistically significant information for the population using methods known in the art. Further a person skilled in the art would know how to calculate iodine levels to determine deficiency/sufficiency in a population using methods known in the art. In some embodiments, the iodide and optionally iodide inhibitor content, obtained from a subject in a population using a method of the application is entered into a computer-based epidemiologic database.

In some embodiments, the subject is human or animal.

In some embodiments, the subject has an iodide deficiency disorder. In some embodiments, the iodide deficiency disorder is selected from impaired cognitive development in children, weight gain, depression, thyroid-related disorders and cardiovascular diseases.

In some embodiments, the method further comprises monitoring iodine deficiency in a population by determining iodide uptake inhibitor content in a sample using a method as defined in the application.

In some embodiments, the methods of the present application are used for population-based nutritional iodine status screening or assessment in epidemiological studies. An iodide assay that provides additional insight into iodide uptake inhibitors, without increasing cost or time demands thus offers "added-value" to epidemiological studies. The methods of the present application therefore offer reliable and cost-effective approaches for on-going surveillance of iodine sufficiency by public health agencies to ensure optimum iodine nutrition in the population.

III. Compositions of the Application

The present application also includes a background electrolyte (BGE) composition for sample self-stacking via transient isotachophoresis followed by zonal electrophoresis comprising an effective amount of a hydroxide salt, an effective amount of a complexing agent and an effective amount of an inorganic acid.

In some embodiments, the effective amount of the hydroxide salt is from about 150 mM to about 200 mM. In some embodiments, the effective amount of the hydroxide salt is from about 160 mM to about 190 mM. In some embodiments, the effective amount of the hydroxide salt is about 180 mM. In some embodiments, the hydroxide salt is selected from sodium hydroxide, potassium hydroxide and lithium hydroxide. In some embodiments, the hydroxide salt is lithium hydroxide.

In some embodiments, the effective amount of the complexation agent is from about 30 mM to about 60 mM. In some embodiments, the effective amount of the complexation agent is from about 30 mM to about 50 mM. In some embodiments, the effective amount of the complexation agent is about 46 mM. In some embodiments, the effective amount of the complexation is about 44 mM. In some embodiments, the effective amount of the complexation agent is about 36 mM. In some embodiments, the complexation agent is selected from iodine/starch, various ionophores for iodide, and α-cyclodextrin. In some embodiments, the complexation agent is α-cyclodextrin.

In some embodiments, the effective amount of the inorganic acid is from about 150 mM to about 200 mM. In some embodiments, the effective amount of the inorganic acid is from about 160 mM to about 190 mM. In some embodiments, the effective amount of the inorganic acid is about 180 mM. In some embodiments, the inorganic acid is phosphoric acid.

In some embodiments, BGE has a pH of 3. The low pH is provided by the acidic buffer (i.e. inorganic acid) which is used to suppress electroosmotic flow (EOF) modifiers while ensuring the inorganic acid exists as the predominant species in solution to function as a TE in transient isotachophoresis.

EXAMPLES

The following non-limiting examples are illustrative of the present application:

Chemicals and Reagents

Potassium iodide, sodium nitrate, lithium hydroxide, α-cyclodextrin, sodium sulfate decahydrate, ammonium chloride, sodium chloride, calcium chloride dehydrate, sodium phosphate monobasic monohydrate, potassium chloride, 1,5-naphthalenedisulfonic acid disodium salt hydrate (NDS), sodium hydroxide, and hydrobromic acid were purchased from Sigma-Aldrich (St. Louis, Mo., USA). Phosphoric acid (85%) was obtained from Fisher Scientific Canada, and magnesium sulfate anhydrous was purchased from Anachemia (Montreal, QC, Canada). Stock solutions of iodide were prepared by dissolving potassium iodide in de-ionized water (Barnstead EASYpure II LF system, Dubuque, Iowa, USA) at the concentration of 50 mM. Stock solutions of bromide (100 mM) were prepared from hydrobromic acid, while chloride (1 M) and nitrate (100 mM) solutions were prepared from their sodium salts. A simulated urine solution was prepared for external calibration, containing 30 mM of potassium chloride, 60 mM of sodium chloride, 2 mM of magnesium sulfate, 13 mM of sodium sulfate, 5 mM of sodium phosphate, 4 mM of calcium chloride, and 15 mM of ammonium chloride, with pH adjusted to 6.0 using 0.1 M sodium hydroxide. This solution mimics the main electrolyte composition of urine, resulting in peak shapes and migration times for iodide and NDS that are comparable to authentic human urine samples.

Example 1: Design, Development and Evaluation of the CE Assay for Detecting Iodide and Iodide Uptake Inhibitors in Human Urine and Human Sweat Samples All analyses were performed in a P/ACE MDQ system with photodiode array detector from Beckman-Counter (Fullerton, Calif., USA), using uncoated fused-silica capillaries (Polymicro Technologies, Phoenix, Ariz., USA) with 75 μm internal diameter, 60 cm of total length and 50 cm of length to the detector. New capillaries were conditioned with methanol for 5 min, followed by deionized water for 5 min and background electrolyte (BGE) for 20 min (20 psi). The BGE was composed of 180 mM lithium hydroxide, 180 mM phosphoric acid and 36 mM α-cyclodextrin (α-CD), pH 3.0, adjusted with 1 M phosphoric acid. In order to ensure a proper and quick solubilisation, the buffer solution was sonicated for 30 s after the addition of phosphoric acid, and for 5 min after the addition of α-cyclodextrin. All the separations were performed at 25° C. using a hydrodynamic injection for 80 s (0.5 psi) under optimum conditions, which is equivalent to about a third of the total capillary length filled with sample. Electrokinetic focusing of trace levels of iodide by sample self-stacking (Gebauer, P. et al. *Electrophoresis* 2000, 21, 2797-2808) was used to achieve adequate sensitivity and linearity for urinary iodide status determination. Reversed polarity was used to allow the selective detection of strong anions using an applied voltage of −18 kV (anode in the capillary outlet) with UV detection at 226 nm (iodide maximum absorbance) and 288 nm (more selective wavelength for the internal standard, NDS). The capillary was rinsed with BGE for 15 min (20 psi) each morning before analysis, and for 3 min (20 psi) prior to each separation. For overnight storage, the capillary was rinsed with de-ionized water for 10 min and kept in vials containing de-ionized water.

(i) Determination of Binding Constant of Strong Anions with α-Cyclodextrin

Nine BGE solutions containing 180 mM lithium hydroxide, 180 mM phosphoric acid, pH 3.0 adjusted with 1 M phosphoric acid were prepared with different concentrations of α-CD (0-70 mM). A standard solution composed of 10 μM iodide, 100 μM thiocyanate, 100 μM bromide, 500 μM nitrate and 20 μM NDS was prepared in de-ionized water and analyzed in triplicate using a normal hydrodynamic injection (5 s at 0.5 psi) under reversed polarity (−18 kV). Since higher α-CD concentrations increase the BGE viscosity, this results in non-specific changes in apparent analyte mobility unrelated to binding. In order to correct for this effect, relative viscosity (v) measurements were performed for each solution by calculating the ratio of the current for the BGE without α-CD ($I_0$) and the current for each other α-CD concentration ($I_i$). Viscosity-corrected electrophoretic mobilities ($\nu\mu_{ep,A} = \mu_{ep,A} \times I_0/I_t$) of iodide, thiocyanate, nitrate, bromide and NDS were thus plotted as a function of α-CD concentration for binding isotherms. A non-linear regression was performed using Igor Pro 5.0 (Wavemetrics Inc., Lake Oswego, Oreg.) to determine the apparent binding constant ($K_b$) and the mobility of the iodide:α-CD complex ($\mu_{ep,Ac}$) assuming a 1:1 dynamic complexation model according to equation (1), where $\nu\mu_{ep,A}$ is the viscosity-corrected apparent electrophoretic mobility of analyte and C is the α-CD concentration.

$$\nu\mu_{ep,A} = \frac{1}{1 + K_b \times C} + \frac{K_b \times C}{1 + K_b \times C} \times \mu_{ep,AC} \quad (1)$$

Sample storage and workup of human urine and other biological fluids. For method development and validation, single-spot urine samples were donated by healthy volunteers, whereas pooled 24 h samples were prepared by combining equal volumes of urine samples from thirty (n=30) or 800 (n=800) gender-matched Canadian adults with a median age of 61 years from four regional centres across Canada, which were collected as part of the Prospective Urban and Rural Epidemiological (PURE) study (Teo, K. et al. *Am Heart J.* 2009, 158:1-7). A standard reference material for iodide, thiocyanate and nitrate in frozen human urine (SRM 3668), was purchased from NIST (Atlanta, Ga., USA) and used for external method validation when comparing CE-derived results with independently measured urinary concentrations using inductively coupled plasma-mass spectrometry (ICP-MS) for iodide, and ion-exchange chromatography-ICP-MS for thiocyanate and nitrate. Samples were stored in a −80° C. freezer in 1.5 mL centrifuge tubes, unless otherwise stated. Frozen samples were allowed to thaw at room temperature for approximately 1 h before preparation. All sample tubes were homogenized by gently inverting several times before volume measurement. A 50 μL aliquot of urine was then transferred to a 0.5 mL centrifuge tube, where 4 μL of 1 mM NDS (final concentration of 20 μM) and 46 μL of de-ionized water were added, resulting in a 2-fold dilution of original urine sample. Urine volumes as low as 10 μL can also be routinely analyzed. The mixture was vortexed for 30 s and centrifuged at 14,000 g for 5 min to sediment any particulates in diluted urine samples. A 40-μL aliquot of the supernatant was then analyzed by CE with UV detection at 226 nm. Overall, the method was able to tolerate urine matrices that vary between-subjects due to large differences in hydration status and diet, which may impact sample self-stacking performance due to differences in conductivity that alter electric field strength when using long sample injection plugs. In most cases, the dilution was minimized to 1.5-fold in order to allow the quantification of iodide below the LOQ. Concentrated urine specimens with high conductivity, however, needed further dilution in de-ionized water (2-fold) in order to maintain resolution of iodide from other interferences due to changes in electromigration behavior. Samples containing extremely high levels of iodide (>6 μM) also needed further dilution (4-fold or more) when concentration levels exceeded the maximum linear range for calibration using the simulated urine matrix, which helps to maintain minimum chloride levels for sample self-stacking with a stable current during separation (120 μA).

This CE assay was also applied to human sweat, which is a secondary route of iodine excretion. Sweat samples (n=3) were collected from patients at the Cystic Fibrosis Clinic at McMaster University, using pilocarpine iontophoresis to stimulate sweat production, and a coiled microbore tube to collect the samples (Webster Model 3700 Macroduct Sweat Capillary Collection System, Wescor Inc., Logan, Utah). Remaining sweat samples after routine analysis at the McMaster Children's Hospital were kept frozen at −20° C. before iodide analysis (Macedo, A. et al. *Anal. Chem.* 2013, 85, 11112-11120). A 10 μL aliquot of sweat was 2-fold diluted in simulated urine, containing NDS to produce a final concentration of 20 μM. After homogenizing by vortex for 30 s, the samples were analyzed directly by CE with UV detection.

(ii) Method Calibration and Assay Validation

Calibration standards at seven different concentrations of iodide (0.20-4.00 μM), thiocyanate (1.00-16.00 μM), and nitrate (50-500 μM) were prepared in triplicate in a 1:1 v mixture of simulated urine matrix and deionized water, using 20 μM NDS as an internal standard. External calibration curves were modeled using linear least squares regression, where linearity was evaluated by the coefficient of determination ($R^2$) and residuals plot, and the percentage relative error (Σ>% RE) throughout the calibration range. The limit of detection (S/N≈3) and limit of quantification (S/N≈10) were determined from the signal of a serially diluted iodide urine sample relative to the background noise measured near the iodide migration time. Accuracy was evaluated through spike-recovery experiments performed in triplicate using a pooled 24 h urine sample derived from 800 subjects from the PURE study at three concentration levels with iodide (0.50, 1.00, and 2.00 μM) and thiocyanate (4.00, 8.00, and 12.00 μM). Additional accuracy tests were performed using a standard urine reference material (SRM 3668) from the National Institute of Standards and Technology (NIST), consisting in two concentration levels for iodide, thiocyanate, and nitrate. The results obtained for the frozen NIST urine standards, analyzed in triplicate over three days (n=9), were compared with the reference anion concentrations, and reported in terms of percent bias. Intra-day precision (repeatability) was evaluated for 10 replicate injections of a pooled 24 h urine sample analyzed within a single day based on the coefficient of variation (CV) for relative peak areas (RPA) and relative migration times (RMT), where anion responses or migration times were normalized to the internal standard, NDS. For inter-day precision, NIST standard reference material (SRM 3668), with two concentration levels of iodide, thiocyanate, and nitrate, was analyzed in triplicate over three days, evaluating the CV for RPA and RMT. Iodide stability was tested using a freshly collected spot urine sample, which was divided into individual aliquots for room temperature and freeze-thaw stability tests, as well as an immediate analysis, used as a control. Samples kept at room temperature (≈25° C.) were analyzed at each 40 min for up to 7 h. For freeze-thaw stability, samples were stored in a −80° C. freezer and were exposed to up to four freeze-thaw cycles, before being analyzed in triplicate. Stability was evaluated as the concentration of iodide in each test relative to the concentration measured in the freshly analyzed urine aliquot. Selectivity was tested in a pooled 24 h urine sample by using a BGE without α-CD and by selective precipitation of iodide using 50 μM silver nitrate. Other UV-active strong anions present in urine were also spiked into the sample to confirm their resolution from iodide, including oxalate, citrate, iodate, thiosulfate, nitrate, nitrite and bromide. Data processing and linear regressions were performed using Igor Pro 5.0 (Wavemetrics Inc., Lake Oswego, Oreg.).

(iii) Robustness and Intermediate Precision Assessment of CE Assay

Robustness and intermediate precision were evaluated over five weeks, using a new capillary and new BGE batch each week, with analysis performed by a single analyst. Electrodes were cleaned every morning before starting the analysis, using a cleaning paper damped with deionized water, in order to prevent urine and salt deposits accumulating that can risk current discharge or sample contamination. A blank solution, composed of simulated urine and NDS in de-ionized water, was first analyzed by CE-UV to check the absence of sample carry-over each morning. Then a calibrant solution with a known concentration of iodide was injected to check the detector response daily, whereas an external calibration curve was generated on a weekly basis by analyzing six different iodide standard solutions each week. This allowed for evaluation of method robustness when comparing the sensitivity and linearity of the method over a five-week period. A quality control (QC, pooled 24 h urine sample prepared from thirty subjects, n=30) reference sample was prepared on the first day of analysis and divided into individual aliquots, which were stored in a −80° C. freezer. One aliquot of QC sample was thawed daily, diluted, and injected intermittently after a block of 10 individual urine samples (≈2.5 hrs), resulting in three QC runs per days (n=3×29 days), for assessment of intermediate precision for a total of 87 runs over 5 weeks of analysis using the same CE instrument.

Figure 2A:
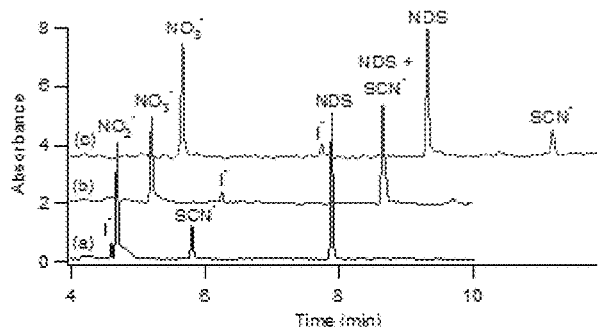
FIGS. 2A and 2B show electropherogram overlays displaying the impact of varying concentrations of α-CD for the separation of bromide, nitrate, iodide, thiocyanate and NDS at 226 nm and at 214 nm, respectively, and FIG. 2C graphically displays a binding isotherm of the viscosity-corrected electrophoretic mobilities of the anions as a function of α-CD concentration in exemplary embodiments of the application.
Figure 2B:
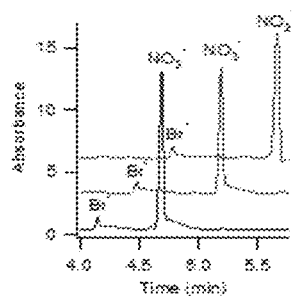

Results (i) Determination of Binding Constant of Strong Anions with α-Cyclodextrin The impact of α-cyclodextrin (α-CD) on the efficient separation of a standard solution containing bromide, nitrate, iodide, thiocyanate and NDS was investigated. Concentrations of α-CD were tested at (a) 10 mM, (b) 40 mM, and (c) 70 mM in the BGE and the standard solution contained bromide at 100 μM, nitrate at 500 μM, iodide at 10 μM, thiocyanate at 100 μM, and NDS at 20 μM. The standard solution was prepared in water and hydrodynamicaly injected for 5 s (at 0.5 psi). Measurements were recorded at 226 nm (FIG. 2A) and 214 nm (FIG. 2B). Bromide has weak absorbance at 226 nm (maximum absorbance optimum for iodide), but is detectable at 214 nm.

Figure 2C:
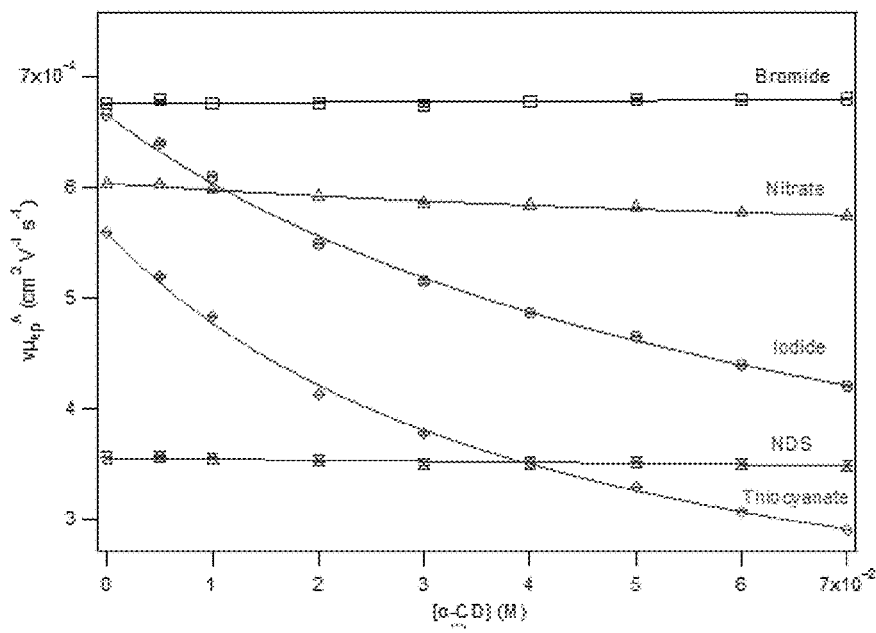

A binding isotherm was generated showing the viscosity-corrected electrophoretic mobilities ($v\mu_{ep}^A$) of the anions as a function of α-CD concentration in the BGE (FIG. 2C). Bromide, NDS and nitrate have negligible interactions with α-CD, whereas iodide and thiocyanate have apparent binding constants of $K_b=(15\pm2)$ $M^{-1}$ and $K_b=(24\pm2)$ $M^{-1}$, respectively. These binding constants are comparable with data reported by Gelb et al. (J. Phys. Chem. 1983, 87, 3349-3354).

(ii) Method Calibration and Assay Validation

Calibration Curves

External calibration curves and residual plots for iodide (0.20-4.00 μM, FIG. 3A), thiocyanate (1.00-16.00 μM, FIG. 3B), and nitrate (50-500 μM, FIG. 3C) were investigated as a function of analyte concentration. Solutions were prepared in triplicate, in a 1:1 v mixture of simulated urine matrix and deionized water, containing 20 μM NDS as internal standard.

A linear increase was determined in measured responses (i.e., relative peak area, RPA) as a function of analyte concentration. Determination coefficients ($R^2$) were >0.999, which shows excellent linearity for all the three anions. Although the residual plots presented values scattered both above and below the zero line throughout all the calibration range, there was a trend for larger variance at higher concentration levels. For this reason, weighted linear least squares regression was evaluated as an option to counteract the possible excessive influence of larger concentrations. However, unweighted linear least squares regression was preferred, as it produced similar slopes and y-intercepts in comparison with weighted least squares, with equal (for iodide and nitrate) or even better (for thiocyanate) sum of percentage relative error (Σ% RE), as compared to weighted linear least squares. In all cases, % RE was below 14% for the LOQ and other concentration levels, which is a good indicator of the model goodness of fit (Almeida et al. J. Chromatogr. B 2002, 774, 215-222).

Optimal Injection Times

The optimal injection times of the sample solutions were investigated to achieve the best resolution of iodide and iodide uptake inhibitors. All samples were prepared in a simulated urine matrix solution diluted 1:1 in de-ionized water. The standard solutions comprised 10 μM iodide and 20 μM thiocyanate and the solutions were injected at time intervals of 5 to 120 s at 0.5 psi.

Figure 4A:
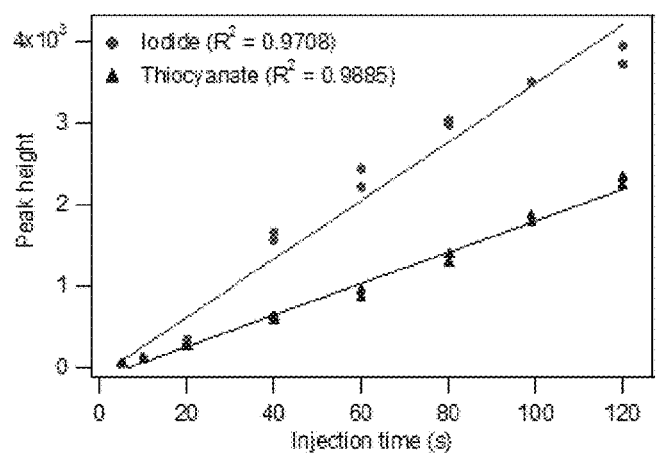
FIG. 4A shows peak height of a standard solution comprised of iodide and thiocyanate as a function of hydrodynamic injection length.
Figure 4B:
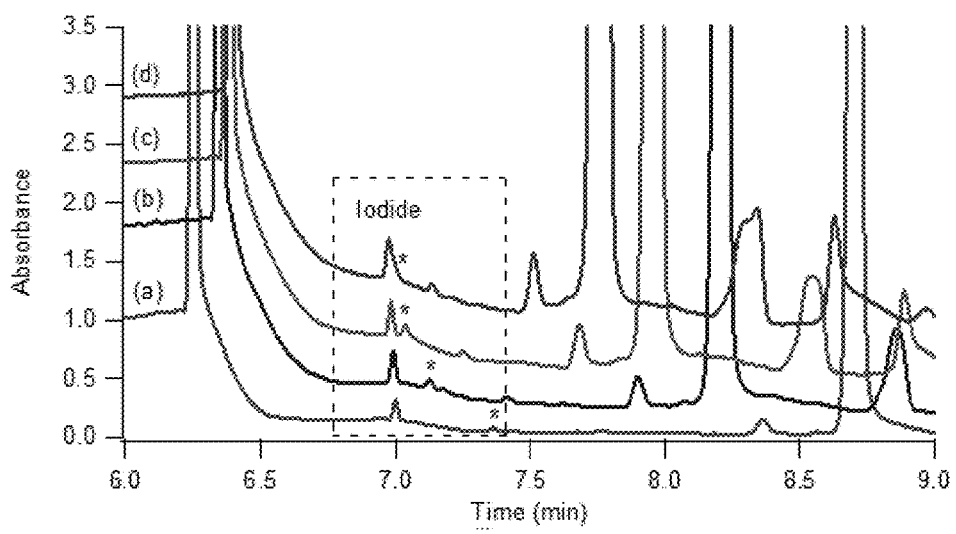
FIG. 4B depicts an electropherogram overlay displaying resolution of iodide with various injection lengths in exemplary embodiments of the application.

A linear increase in peak height was measured for the standard solution as a function of hydrodynamic injection length (from 5 to 120 s at 0.5 psi) when using sample self-stacking in CE with UV detection (FIG. 4A). Although there is a continuous increase in absorbance response (226 nm) for iodide (and thiocyanate) without significant band broadening in standard solutions, resolution is compromised when using injections longer than 80 s for human urine specimens, as shown in the electropherogram overlay of a 2-fold diluted random spot urine sample containing 2.34 μM iodide (FIG. 4B). The resolution between iodide and an unknown interference in urine (indicated by asterisk) is adequate for (a) 40 s and (b) 80 s injections, but becomes problematic when the injection time increases to (c) 100 s with co-migration at d) 120 s injection. Loss of resolution with longer sample injection times is a result of filling a major portion of the capillary with urine, which results in a shorter effective capillary length for separation (120 s injection, for example, corresponds to ≈50% of the total capillary length, 60 cm). For this reason, an optimum sample loading of 80 s (≈34% of the capillary length) was used in our work as it represents a compromise between sensitivity gain with resolution needed for reliable urinary iodide analysis.

Selectivity for Iodide

A pooled 24 h urine sample (n=800) was diluted 2-fold in de-ionized water and naphthalene disulfonate (NDS). The sample was run through capillary electrophoresis wherein the conditions comprised i) fused-silica capillary with 75 μm i.d., total length of 60 cm, 50 cm to the detector; ii) buffer/background electrolyte (BGE) is composed of 180 mM lithium hydroxide, 180 mM phosphoric acid and 36 mM α-CD, pH 3.0 adjusted with 1 M phosphoric acid; and a sample injection of 80 s (0.5 psi); reversed polarity (−18 kV); and detection at 226 nm. Similar conditions were used for a blank sample composed of simulated urine with NDS (no signal for iodide and thiocyanate, with a residual nitrate signal due to salt impurities in sample, FIG. 2B).

Figure 5A:
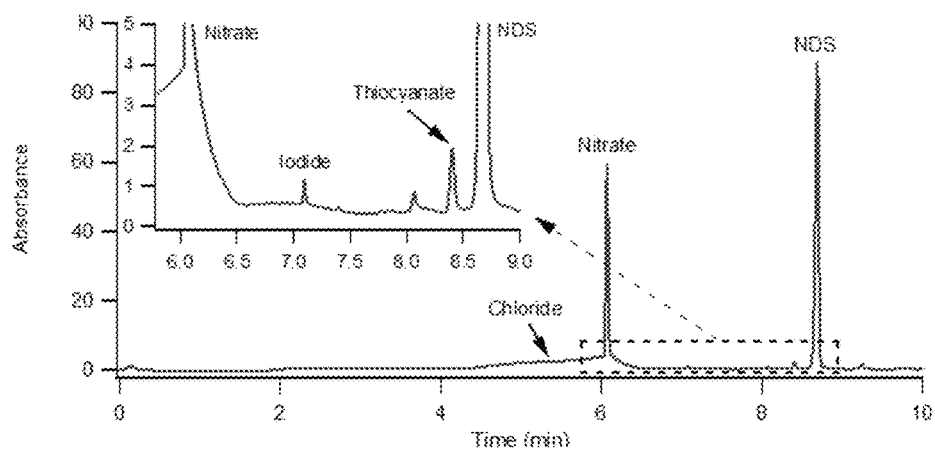
FIG. 5A shows an electropherogram of a pooled 24 h urine sample.

FIG. 5A illustrates the electropherogram for the pooled 24 h urine sample (n=800). Selectivity for iodide, thiocyanate and nitrate was tested by treating the urine sample with silver chloride to precipitate iodide (FIG. 5B, (c)) and by using a BGE without α-CD (FIG. 5B, (d)) resulting in the co-migration of iodide as a broad zone with chloride without sample self-stacking, whereas thiocyanate co-migrates with nitrate.

Limit of Quantification (LOQ) of Iodide

The LOQ level of iodide was investigated using the conditions of the CE assay as taught in the previous examples. Sample solutions included a standard solution containing iodide at the LOQ level (0.20 µM, FIG. 6a), as well as representative 24 h urine samples with different concentrations of iodide: 0.30 µM (FIG. 6b), 0.49 µM (FIG. 6c), 0.92 µM (FIG. 6d), 2.30 µM (FIG. 6e), and 3.35 µM (FIG. 6f). Urine samples were diluted 1.5-fold in deionized water with 20 µM NDS as internal standard. These representative iodide levels span the major categories of iodide nutritional status according to the World Health Organization (WHO, *Assessment of iodine deficiency disorders and monitoring their elimination: a guide for programme managers*; Geneva, 2007), including moderate deficiency (0.16-0.38 µM), mild deficiency (0.39-0.78 µM), adequate intake (0.79-1.57 µM), more than adequate (1.58-2.36 µM) and excessive intake 2.37 µM).

Apparent migration times for iodide were found to vary considerably (CV=1.8% for five 24 h urine samples), due to variations in the ionic strength/conductivity of urine samples as a result of between-subject differences in hydration status/diet, however this does not impact iodide peak identification nor quantification. The use of relative migration times (RMTs) helps to improve the precision of the migration behaviour (CV=1.4% for iodide RMT in five 24 h urine samples), even though in this case the improvement is only moderate, as a result of the difference between the migration times of iodide and NDS (>1.4 min).

Effect of Dilutions on Conductivity

Electropherograms were generated showing adjustments in sample dilution for specific urine samples (left y-axis, continuous trace) and the variability in the resultant current (right y-axis, dashed trace under reversed polarity). Between-subject variations in 24 h urine samples analyzed reflect differences in hydration status and diet that alters urine conductivity that can impact CE separation performance.

Figure 7A:
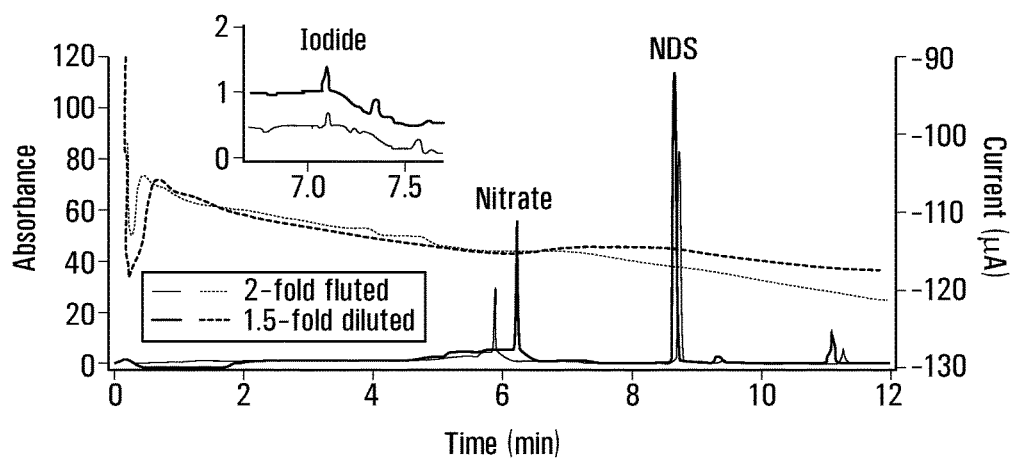
FIGS. 7A, 7B and 7C show electropherogram overlays displaying adjustments in sample dilution for specific urine samples and the variability in the resultant current in exemplary embodiments of the application.
Figure 7B:
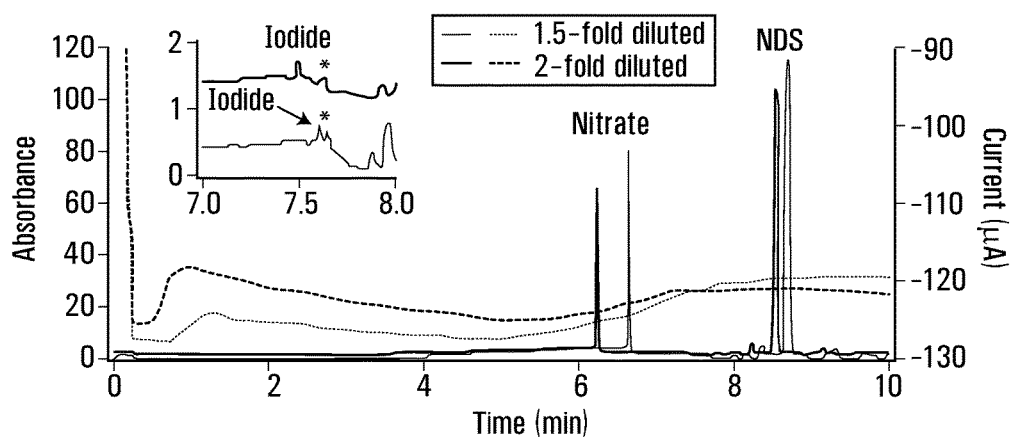
Figure 7C:
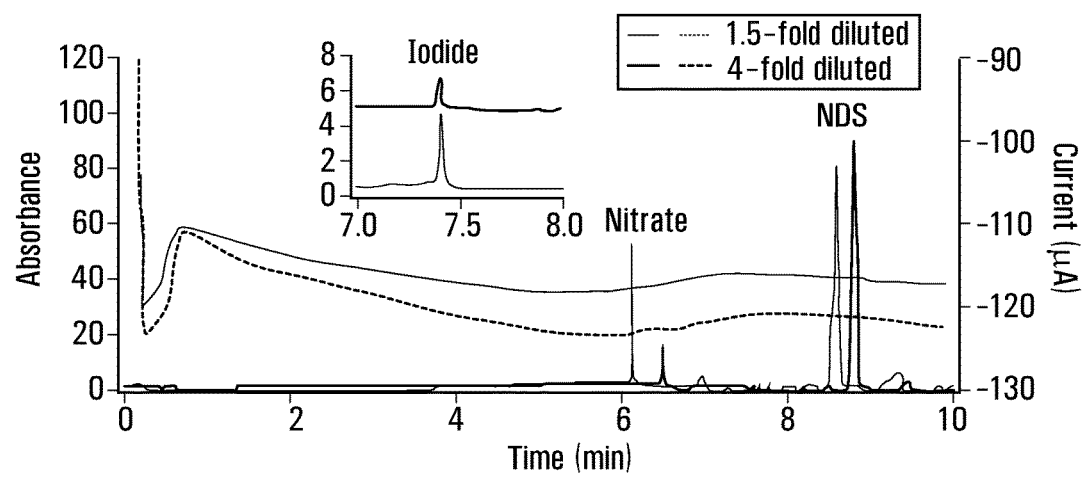

Overall, the separation current was found not to be constant over the entire run due to the large sample injection of minimally diluted human urine as required for on-line sample preconcentration in CE. For instance, some individual 24 h urine samples in which iodide was slightly below the LOQ when the samples were 2-fold diluted, could be quantified by minimizing dilution to 1.5-fold (FIG. 7A). While 1.5-fold dilution works well for the majority of urine samples examined in our study (>92% of 800×24 h urine samples), it can affect the resolution between iodide and an interference present in the urine matrix (indicated with asterisk) for some samples with very high ionic strength/conductivity with current that surpasses 125 µA (FIG. 7B). In these cases, the problem is solved by simply increasing the sample dilution to 2-fold in de-ionized water. Also, in some cases, samples that had a very high excess of iodide in urine, required additional dilution in order to fall within the linear range of method (0.20-4.00 µM), as shown in a urine sample with 10.12 µM iodide (FIG. 7C). In this case, further dilution of 4-fold was performed using a mixture of 1:1 simulated urine in de-ionized water.

Long-Term Variability of Iodide Uptake Inhibitors: Thiocyanate and Nitrate

Figure 8A:
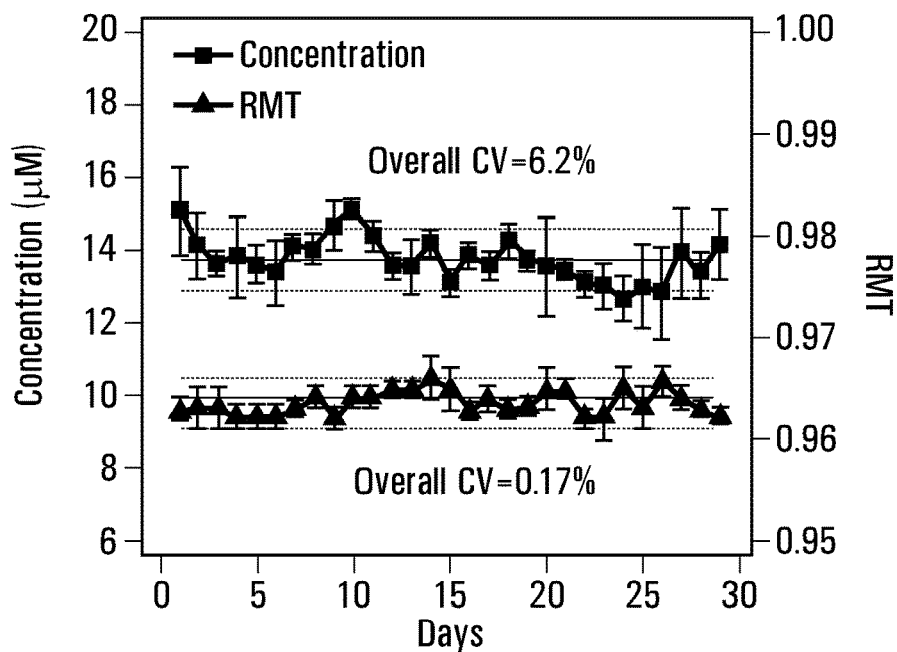
FIGS. 8A and 8B show long-term variability in thiocyanate and nitrate measurements, respectively, derived from a 24 h pooled urine sample analyzed over 29 days in exemplary embodiments of the application.
Figure 8B:
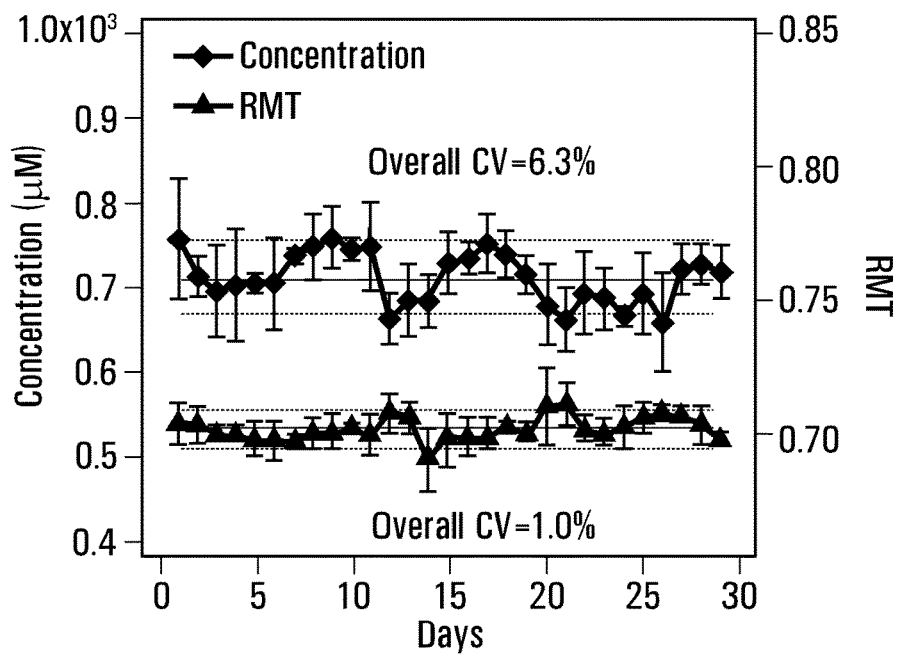

Long-term variability in thiocyanate (FIG. 8A) and nitrate (FIG. 8B) measurements derived from a 24 h pooled urine sample (n=30) were analyzed in triplicate over 29 days (total of 87 runs) using five different capillaries and five batches of BGE throughout the study (on days 1, 8, 14, 20 and 26).

Overall CVs for measured urinary concentrations were 6.2% and 6.3% for thiocyanate and nitrate, respectively. Also, relative migration times (RMTs) had excellent intermediate precision with overall CVs of 0.17% for thiocyanate and 1.0% for nitrate. The better precision measured for the RMT of urinary thiocyanate is due to its close migration time with internal standard. Compared to their inter-day precision (Table 2), thiocyanate and nitrate had similar CVs for concentrations, but higher (yet still acceptable) CVs for RMTs over a longer time period. Error bars represent the standard deviation for the daily replicates, while the solid black lines indicate the overall mean concentrations and RMT of thiocyanate (13.7 µM and RMT=0.963) and nitrate (710 µM and RMT=0.702). Dashed black lines show the interval of the overall mean±standard deviation for concentrations (12.9-14.6 and 666-755 µM for thiocyanate and nitrate, respectively), as well as RMT (0.962-0.965 for thiocyanate and 0.695-0.709 for nitrate). Overall, the CE assay provides excellent long-term stability with adequate robustness for reliable measurements of iodide, as well as two relevant iodide-uptake inhibitors in the environment, namely nitrate and thiocyanate.

Quantification of Iodide in Human Sweat Samples

Electropherograms of three individual sweat samples (FIG. 9) collected by pilocarpine iontophoresis, containing (a) 0.32 µM iodide and 2.34 µM thiocyanate, (b) 0.71 µM iodide and 2.33 µM thiocyanate, and (c) 1.59 µM iodide and 4.83 µM thiocyanate. In this case, nitrate was not quantified due to the application of pilocarpine nitrate as a sweat stimulant before sample collection, so that nitrate present in the sample is not just from endogenous source. Although most iodide is excreted through the urine, sweat is another route of iodide excretion in the human body, which may be of interest especially in studies involving iodide loss in athletes undergoing intense exercise (Smyth, P. P. A.; Duntas, L. H. *Horm. Metab. Res.* 2005, 353, 1-4.).

(iii) Robustness and Intermediate Precision Assessment of CE Assay

Figure 10A:
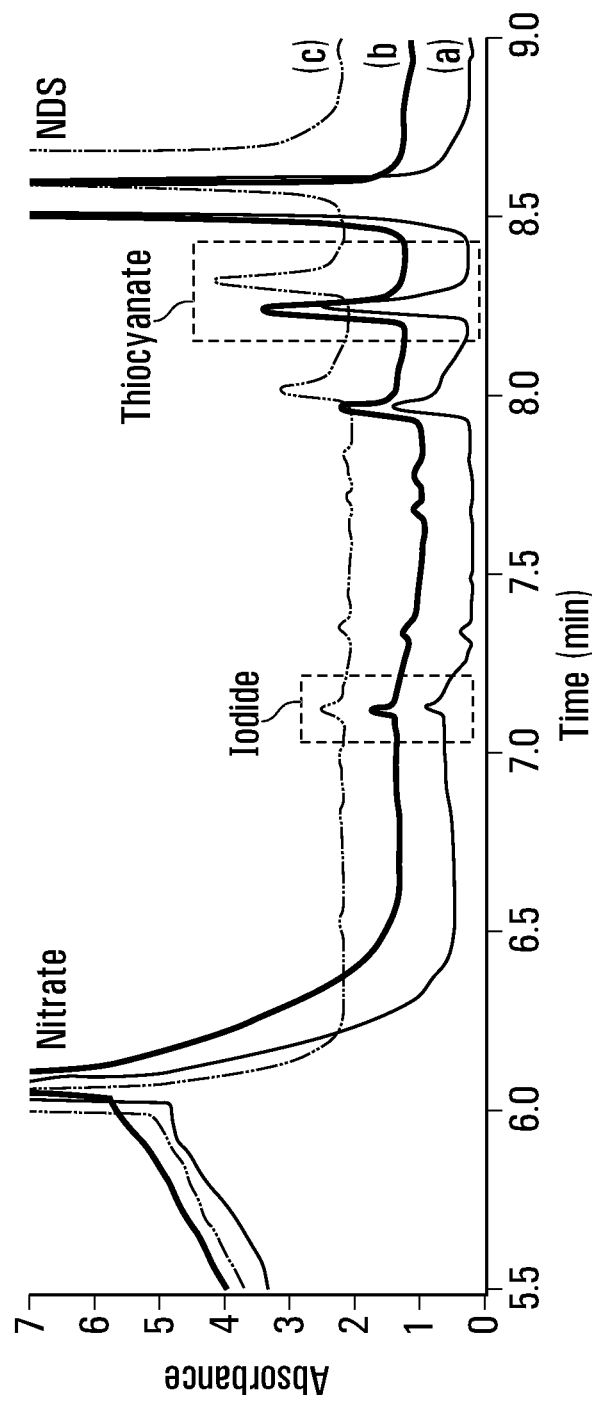
FIG. 10A shows an electropherogram of a pooled 24 h urine sample over 29 days, FIG. 10B graphically depicts the variability within these samples and FIG. 10C graphically displays the calibration curves obtained at 5 consecutive weeks in exemplary embodiments of the application.
Figure 10B:
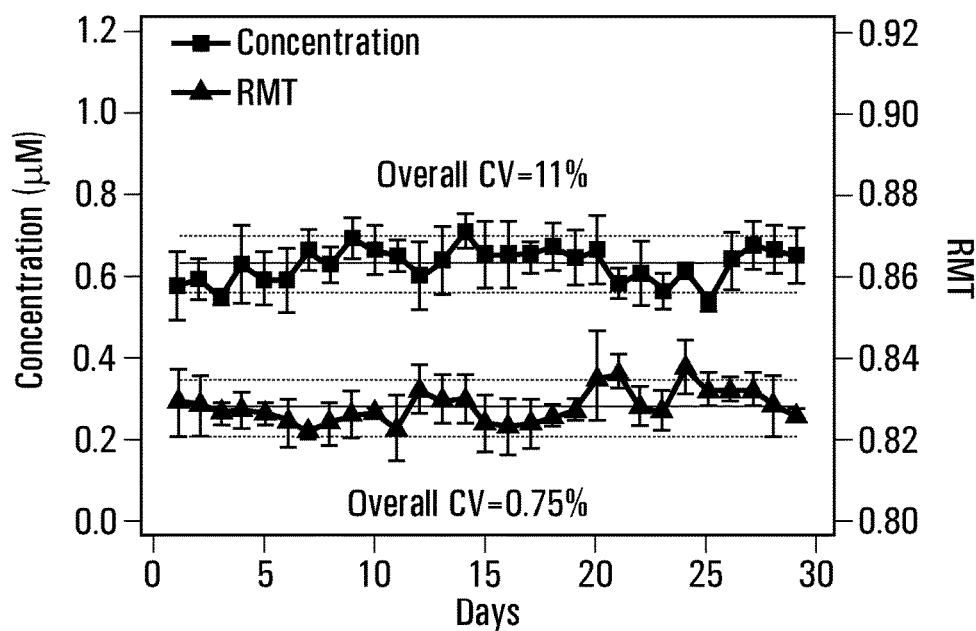

Variability of pooled 24 h urine samples (n=30) were analyzed on the (a) $1^{st}$, (b) $15^{th}$, and (c) $29^{th}$ days (FIG. 10A). The samples were analyzed in triplicate using five different capillaries and five batches of BGE over 29 days (total of 87 runs) (FIG. 10B).

The overall CV for measurement of iodide concentrations was 11%, whereas the relative migration times (RMT) for iodide had an overall CV of 0.75%. Error bars represent the standard deviation (±1σ) for the daily triplicates. The grand means for iodide concentration (0.63 µM) and RMT (0.827) are depicted by solid black lines, whereas dashed black lines represent overall standard deviations (±1σ).

Figure 10C:
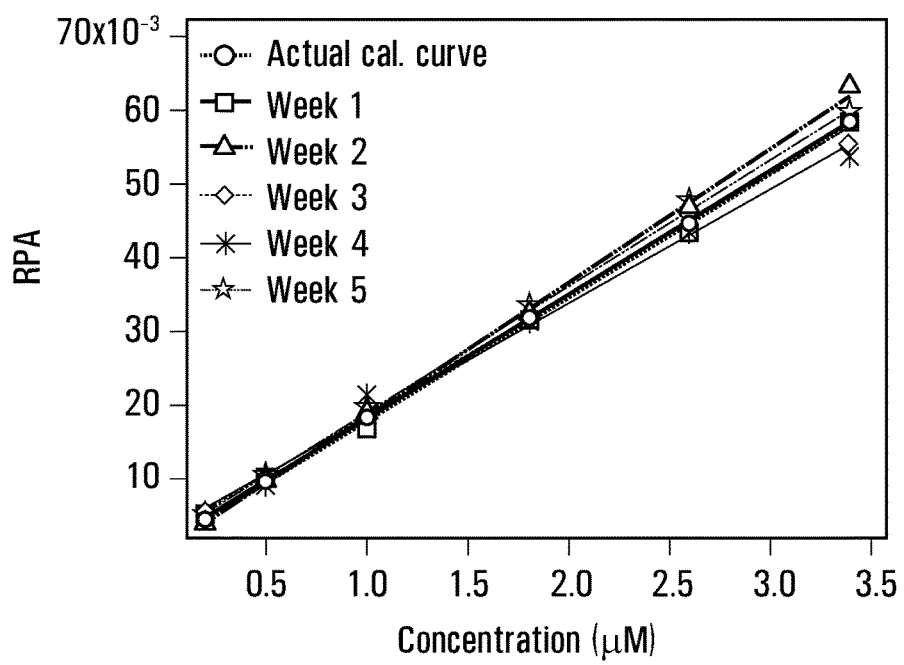

Calibration curves were generated by analyzing one calibrant solution per day each week during study resulting in five independent curves (FIG. 10C). Remarkable consistency was observed when comparing the weekly calibration curves with the original calibration curve prior to start of the study with overall 4% bias and 6% CV in the slope.

Discussion

On-line sample pre-concentration was performed by sample self-stacking,[27] where chloride, naturally present in urine at high concentrations (≈100 mM) serves as the leading electrolyte (LE), whereas the background electrolyte (BGE) is composed of a slow-mobility anion (dihydrogen phosphate) that acts as buffer and terminating electrolyte (TE). FIG. 1 shows a schematic of the separation configuration used in CE, which offers a simpler and more effective approach for routine analysis of urinary iodide than previous tITP formats. For instance, the strategy of the present application avoids the use of various TEs injected as a segment after the sample and the addition of high concentrations of chloride to the BGE for matrix matching, which limits electric field strength resulting in longer analysis times.[20,22-24] However, sample self-stacking requires the analyte to migrate with an intermediate electrophoretic mobility ($\mu_A$), relative to the LE ($\mu_{LE}$) and TE ($\mu_{TE}$). Since free iodide has a similar mobility to chloride in aqueous solution, dynamic inclusion complexation using a complexing agent, such as α-cyclodextrin (α-CD), is critical for resolving trace levels of iodide in urine while also providing the necessary conditions for sample self-stacking, since the mobility of the iodide: α-CD complex is slower than chloride, but still faster than dihydrogen phosphate. For instance, α-CD interacts differentially with inorganic anions,[28,29] including iodide and thiocyanate, whose binding constants ($K_b$) derived from viscosity-corrected mobility binding isotherms were measured as (15±2) $M^{-1}$ and (24±2) $M^{-1}$, respectively. In contrast, chloride, bromide, and nitrate were found to have negligible binding to α-CD (FIG. 2).

Cationic surfactants have been largely used as additives to modulate iodide mobility in CE,[20,22,24] however they also have a major impact on the separation performance as strong electroosmotic flow (EOF) modifiers. As presently disclosed, an acidic buffer condition (pH 3) is used to suppress the EOF while ensuring dihydrogen phosphate exists as the predominate species in solution. A critical aspect to separation optimization was the use of a high ionic strength BGE/TE (180 mM), in order to ensure good sample self-stacking performance for trace levels of iodide in the presence of up to a $10^5$-fold excess of chloride in minimally diluted human urine. Also, lithium was selected as the counter-ion in order to reduce solution conductivity and Joule heating effects.

Overall, 36 mM α-CD was used in the BGE in order to achieve on-line sample pre-concentration of iodide and its resolution from other more abundant urinary interferences. Under these conditions, there was a linear increase in iodide response with longer hydrodynamic injections up to 80 s (0.5 psi) while maintaining resolution that is equivalent to a urine sample filling approximately 34% of the total capillary length (FIG. 4).

FIG. 5A shows a representative electropherogram for a pooled 24 h urine sample (n=800) diluted 2-fold in deionized water after a centrifugation to sediment particulates. Naphthalene disulfonate (NDS) is included as an internal standard to improve migration time precision and quantitative performance due to run-to-run variations in EOF and sample injection volume, respectively. The average concentrations for iodide, thiocyanate and nitrate in a pooled urine sample collected from an adult population across Canada, were measured to be (1.47±0.05) μM, (19.5±1.2) μM and (968±29) μM, respectively. Iodide levels are within the range of adequate iodine intake (0.78-1.47 μM),[3] which is consistent with recent literature the Canadian Health Measures Survey reporting a geometric mean of 1.01 μM.[30] Also, the US National Health and Nutrition Examination Survey (NHANES) reports comparable urinary concentration levels in an adult population with geometric means of 1.29 μM iodide, 26.2 μM thiocyanate, and 814 μM nitrate.[31]

Other UV-absorbing strong anions (e.g., iodate, thiocyanate, thiosulfate, oxalate, nitrite, and citrate) spiked into urine did not interfere with iodide. Also, iodide was found to be stable in freshly collected random spot urine samples for at least 7 h at room temperature, as well as after four consecutive freeze/thaw cycles (Table 1).

TABLE 1

Stability tests for iodide and thiocyanate in urine, after storage at room temperature (≈25° C.) or multiple freeze-thaw cycles, represented as the recovery (%) relative to the results obtained for the freshly collected sample.

| Freeze-thaw stability | | | Room temperature stability | | |
|---|---|---|---|---|---|
| Cycles | Iodide | Thiocyanate | Hours | Iodide | Thiocyanate |
| 1 | 98 ± 1 | 93 ± 6 | 1 | 98 | 103 |
| 2 | 97 ± 3 | 95 ± 14 | 2 | 98 | 92 |
| 3 | 101 ± 6 | 95 ± 2 | 4 | 101 | 109 |
| 4 | 99 ± 7 | 102 ± 2 | 7 | 104 | 95 |

Figure 5B:
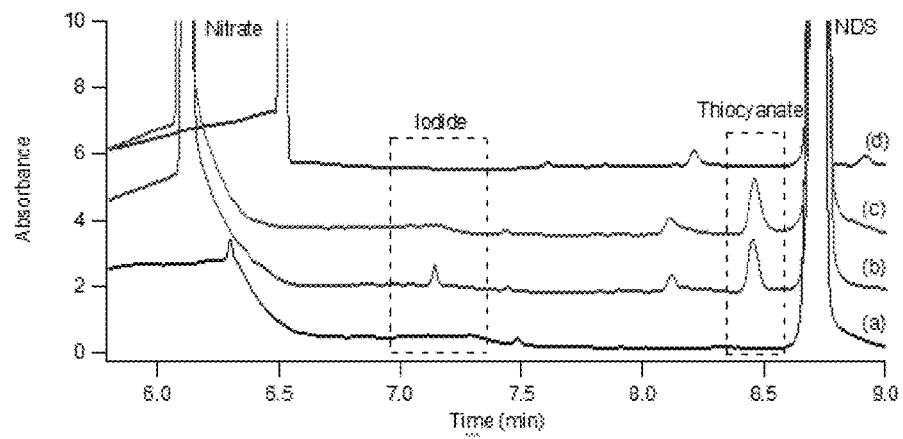
FIG. 5B shows an electropherogram of a a) blank sample, b) pooled 24 h urine sample, c) urine sample with iodide precipitated and d) urine sample without α-CD in exemplary embodiments of the application.

Selectivity was further evaluated by analyzing a urine specimen using a BGE without α-CD (condition in which iodide co-migrates with chloride and the injection band remains broad and unfocused), and using silver ion to precipitate iodide prior to CE analysis (FIG. 5B). In both cases, there was no signal at the relative migration time (RMT) corresponding to iodide in contrast to the same sample spiked with iodide.

Figure 3A:
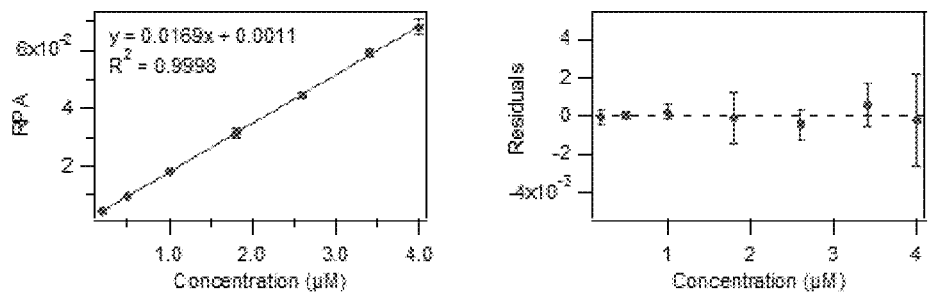
FIGS. 3A, 3B and 3C show external calibration curves and residual plots for iodide, thiocyanate and nitrate, respectively, as a function of analyte concentration in exemplary embodiments of the application.
Figure 3B:
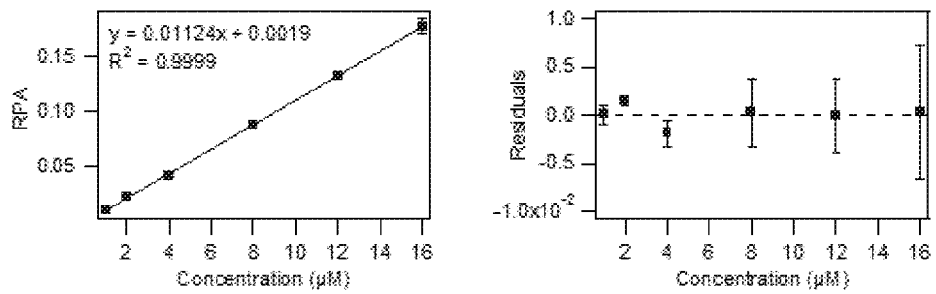
Figure 3C:
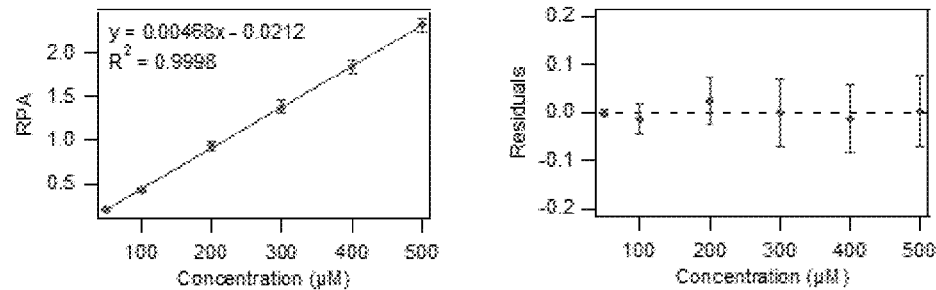

The calibration curve [y=(0.0169±0.0002)x+(0.0011±0.0002), iodide concentration in μM] demonstrated excellent linearity ($R^2$=0.9998) over a 20-fold concentration range (0.20 to 4.00 μM) as required for determination of urinary iodide status (FIG. 3A). In all cases, calibrant solutions were prepared in a simulated urine matrix in order to derive consistent iodide electromigration and sample self-stacking performance relative to authentic urine samples. Calibration curves and residual plots for thiocyanate and nitrate are also depicted in FIGS. 3B and 3C. Intra-day and inter-day precision measured for iodide had maximum coefficient of variance (CV) of 7.4% based on relative peak areas, and 0.71% for RMT (Table 2).

TABLE 2

Inter-day and intra-day precision for relative peak areas (RPA) and relative migration times (RMT) of iodide, thiocyanate, and nitrate in pooled 24 h urine by CE with UV detection.

| | Intra-day precision (n = 10) | | | Inter-day precision (n = 3 × 3) | | |
|---|---|---|---|---|---|---|
| Anions | Conc. (μM) | RPA (CV, %) | RMT (CV, %) | Conc. (μM) | RPA (CV, %) | RMT (CV, %) |
| Iodide | 1.47 | 3.4 | 0.71 | 1.12 | 7.4 | 0.074 |
| | | | | 2.20 | 5.3 | 0.21 |
| Thiocyanate | 19.5 | 6.0 | 0.074 | 20.0 | 7.2 | 0.050 |
| | | | | 119.1 | 5.6 | 0.055 |
| Nitrate | 977.6 | 3.0 | 0.87 | 624 | 2.6 | 0.12 |
| | | | | 1456 | 5.1 | 0.27 |

Method accuracy, evaluated based on spike-recovery experiments, was performed in triplicate at three different concentration levels, with an average recovery of 93% within the range of 80-110% (Table 3).

TABLE 3

Accuracy based on spike-recovery at three concentration levels analyzed in triplicate, and NIST reference urine sample (SRM 3668) at two concentration levels, analyzed in triplicate over three days.

| | Spike-recovery (n = 3) | | NIST ref. material (n = 9) | |
|---|---|---|---|---|
| Anion | Conc. spiked (μM) | Recovery ± SD (%) | Ref. conc. (μM) | Bias (%) |
| Iodide | 0.50 | 88 ± 9 | 1.12 | 35 |
| | 1.00 | 99 ± 5 | 2.20 | 15 |
| | 2.00 | 93 ± 4 | | |

TABLE 3-continued

Accuracy based on spike-recovery at three concentration levels analyzed in triplicate, and NIST reference urine sample (SRM 3668) at two concentration levels, analyzed in triplicate over three days.

| | Spike-recovery (n = 3) | | NIST ref. material (n = 9) | |
|---|---|---|---|---|
| Anion | Conc. spiked (µM) | Recovery ± SD (%) | Ref. conc. (µM) | Bias (%) |
| Thiocyanate | 4.00 | 100 ± 10 | 20.0 | 23 |
| | 8.00 | 113 ± 16 | 119.1 | 6 |
| | 12.00 | 118 ± 10 | | |
| Nitrate | — | — | 624 | −8 |
| | | | 1456 | −14 |

Accuracy was also tested using NIST reference urine sample (SRM 3668) with results derived from a validated ICP-MS method[32] with an acceptable bias of +15% at a higher iodide level (2.20 µM), but a slightly greater positive bias (+35%) was measured for a urine sample at a lower iodide level (1.12 µM). Decision charts to evaluate method acceptability for iodine deficiency tests rated "world-class" laboratories having a bias under 40% with imprecision at 10%, which are often not satisfied when using conventional colorimetric kinetic methods.[33] Similarly, average bias for urinary thiocyanate and nitrate at two levels was also found to be acceptable with +15% and −12% when comparing CE results with data from ion-exchange chromatography-ICP-MS.

Method robustness was further evaluated by analyzing a pooled 24 h urine sample (n=30) over 29 days, with three replicate runs analyzed intermittently each day between a block of ten individual urine samples when using new capillaries and preparing fresh BGE stock solutions each week along with daily maintenance cleaning of the CE instrument. FIG. 10A depicts representative electropherograms throughout the study period. An overall average CV of 11% (n=87) was derived for quantification of urinary iodide concentrations, which is only marginally higher than the inter-day precision for the NIST standards over 3 days (CV=7.4%, n=9) demonstrating acceptable intermediate precision (FIG. 10B). Excellent long-term RMT precision was also realized for iodide (CV=0.74%) despite changes in fused-silica capillaries and buffer stock solutions over a five-week period. Furthermore, a series of five calibration curves derived from six calibrant solutions measured each day every week show excellent agreement in terms of method sensitivity (<4% bias in slope) and long-term stability on the same instrument (FIG. 10C).

Figure 6:
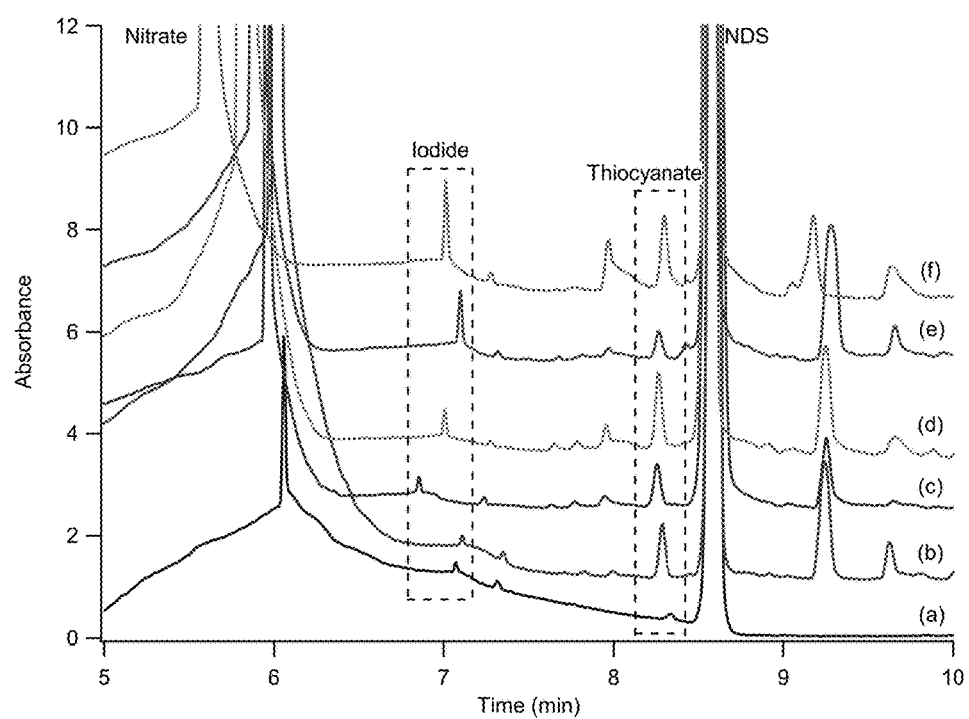
FIG. 6 shows electropherogram overlays displaying application of the CE assay to standard solution with iodide (a) and urine samples with varying concentrations of iodide (b), (c), (d), (e) and (f) in exemplary embodiments of the application.

The validated method was applicable to urine samples with different iodide concentrations, which are representative of the main categories of iodine insufficiency according to the World Health Organization,[3] as shown in FIG. 6. Due to the high ionic strength and buffer capacity of the BGE, sample self-stacking of urine samples was effective for the majority (>92%) of urine specimens examined in our work after a 1.5-fold dilution in de-ionized water, including 800× 24 h urine specimens from the Population Urban Rural Epidemiological (PURE) study.[34] This dilution level was found to be a trade-off between sensitivity and resolution in order to reliably quantify cases of moderate iodide deficiency (<0.2 µM) near the LOQ of the CE method as shown in FIG. 7. In some cases, repeated analysis (<8%) with a two-fold dilution in de-ionized water was required for certain urine samples with excessive iodide levels that exceeded the upper linear range of the method (>8 µM) or concentrated urine samples with high conductivity that altered iodide migration resulting in co-migration with an unknown urine interference.

Overall, the CE method was found to largely tolerate the vast majority of urine matrices collected within a large-scale epidemiological study that vary widely in hydration status and diet. The other strong anions analyzed in the assay, thiocyanate and nitrate, also were found to have acceptable variance (CV<7% for urinary concentration; CV<1% for RMT) as shown in FIG. 8. Both nitrate and thiocyanate are known to inhibit iodide uptake by the thyroid, and thus have been studied in conjunction with iodide in urine and serum.[31,35] Nitrate exposure is typically derived from contaminated drinking water, whereas thiocyanate is a metabolite of cyanide that is derived from smoking and/or the consumption of certain foods, such as cassava.

Figure 9:
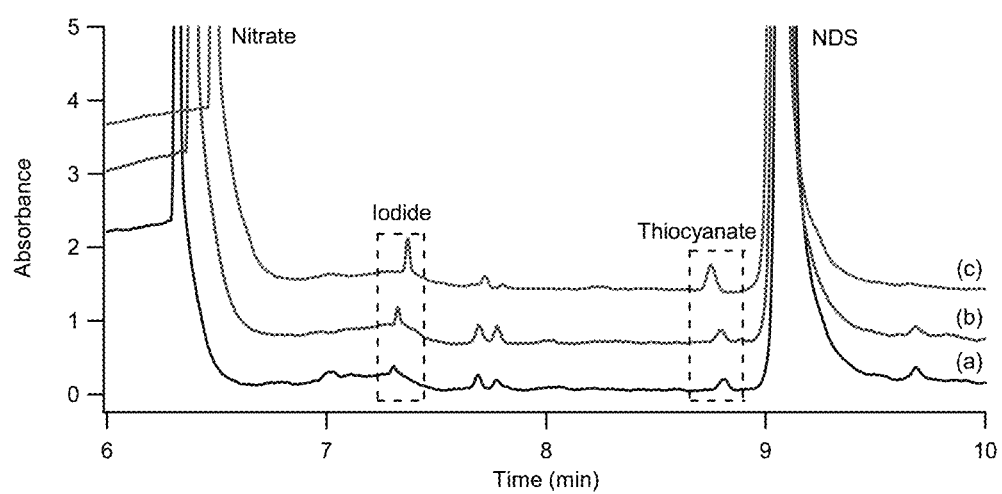
FIG. 9 depicts an electropherogram overlay displaying iodide and thiocyanate concentrations in three individual sweat samples [(a), (b) and (c)] collected using pilocarpine ionophoresis in exemplary embodiments of the application.

An iodide assay that provides additional insight into iodide uptake inhibitors, without increasing cost or time demands thus offers "added-value" to epidemiological studies.[11] Although urinary iodine status was the primary focus of this work, this method is also applicable to iodide, nitrate and/or thiocyanate analysis in other biological specimens, such as human sweat specimens (FIG. 9). For instance, sweat, as a secondary route of iodide elimination in the body, may cause iodine deficiency in athletes undergoing vigorous exercise under hot weather conditions.[36] However, perchlorate, a potent inhibitor of iodide uptake, is not feasible to be analyzed by our method as it is a UV-transparent strong anion, thus requiring CE with indirect UV detection.[26]

In summary, the present application introduces a robust CE assay for iodine status determination suitable for large-scale epidemiological studies as required for global health initiatives. Excellent selectivity and adequate sensitivity are achieved while using a novel on-line sample pre-concentration method based on sample self-stacking that requires only a modest dilution of urine. This method takes advantage of the high saline content in urine specimens, a high ionic strength/acidic lithium phosphate buffer system as BGE, and α-CD as an additive to tune the mobility of iodide (and thiocyanate) using an unmodified fused-silica capillary under reversed polarity. Rigorous method validation demonstrates acceptable accuracy, intermediate precision and linear dynamic range to classify urinary iodide status among diverse urine specimens with excellent long-term stability over five weeks of continuous analysis. Although ICP-MS may provide lower limits of quantification (<0.08 µM), the sensitivity of the CE assay with sample self-stacking is comparable to kinetic spectrophotometric assays (LOQ=0.20-0.39 µM), with similar inter-day precision as both methodologies (CV≈10%).[17,37,38] Major benefits of this assay include greater selectivity for resolution of iodide from other iodine-related drugs/food additive interferences that also permits simultaneous analysis of nitrate and thiocyanate using volume-restricted urine specimens from bio-repositories (≈10 µL) without complicated sample handling. The method can also tolerate large differences in urine conductivity caused by between-subject variations in hydration status that is readily corrected by appropriate dilution or matrix matching. Apart from infrastructure costs for CE instrumentation and lifespan of a deuterium lamp, operational costs for large-scale analyses are minimal (<$1/sample) due to the use of small amount of aqueous buffer and largely inexpensive reagents with a sample throughput of about 100 samples/day, including sample workup.

Example 2: Optimization of the Background Electrolyte Conditions to Tolerate Urinary Sulfate An inter-laboratory method comparison using CE with UV detection and inductively coupled plasma-mass spectrometry (ICP-MS) to quantify iodine status in human urine samples (n=74) was performed both at McMaster University/Hamilton General Hospital, and the Centre for Disease Control in support of their quality assurance program. A positive bias in the conditions of the CE assay of Example 1 was indicated, thus, optimization of the buffer conditions was further investigated to avoid matrix interferences to enable reliable iodide quantification.

Sulfate is known to be a stable anion and unreactive with iodide or with any of the compounds involved in the assay. Sulfate is also UV-transparent, not producing any signal at the wavelength used for iodide detection (i.e. 226 nm). However, sulfate is a major anion present in urine at concentrations that are >5,000-fold in excess to iodide, and it was found to migrate closely to iodide under the conditions exemplified in Example 1. Major co-ion interferences with an effective mobility similar to that of the analyte can impact the efficacy of sample self-stacking and migration times in CE separations.[39]

Therefore, the background electrolyte conditions (BGE) as found in Example 1's CE-UV assay have been modified to account for co-ion interference by sulfate. In particular, $\alpha$-cyclodextrin concentrations have been increased from 36 to 46 mM, in order to tolerate the variable levels of urinary sulfate that was determined as an unanticipated interference of iodide. An increase in the $\alpha$-CD concentration to 46 mM was found to decrease the effective mobility of iodide relative to sulfate to avoid a source of interference.

Figure 11A:
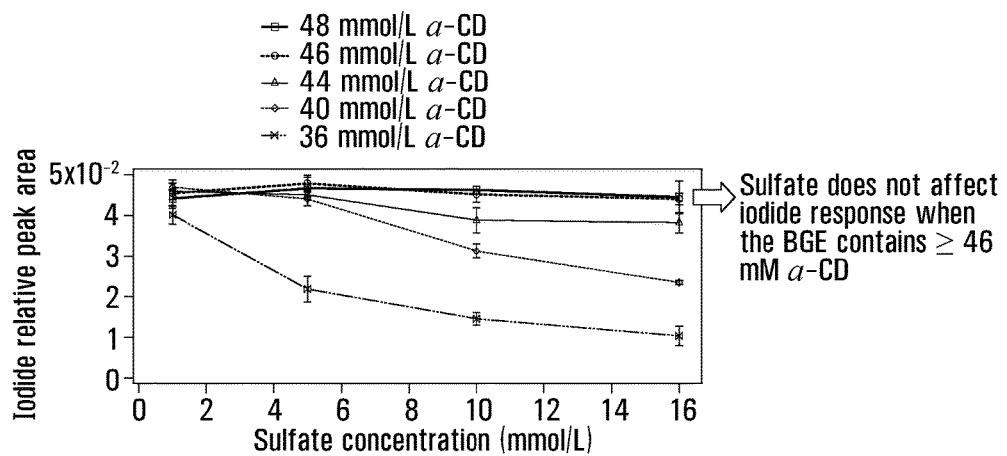
FIG. 11A shows the changes in urinary iodide response measured by CE-UV as a function of sulfate concentration in sample and α-cyclodextrin concentration in the BGE, which clearly shows that the use of 46 mM α-CD decreases attenuation of iodide signal even in the presence of 16 mM sulfate compared to the conditions at 36 mM α-CD in exemplary embodiments of the application.
Figure 11B:
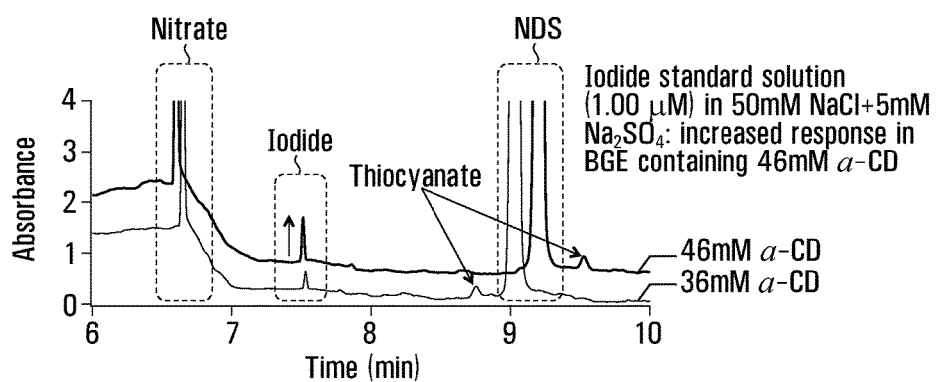
FIG. 11B shows an electropherogram overlay highlighting improved recovery of the iodide signal when using 46 mM α-CD in the BGE without interference from urinary sulfate that occurs when using 36 mM α-CD in exemplary embodiments of the application.
Figure 12A:
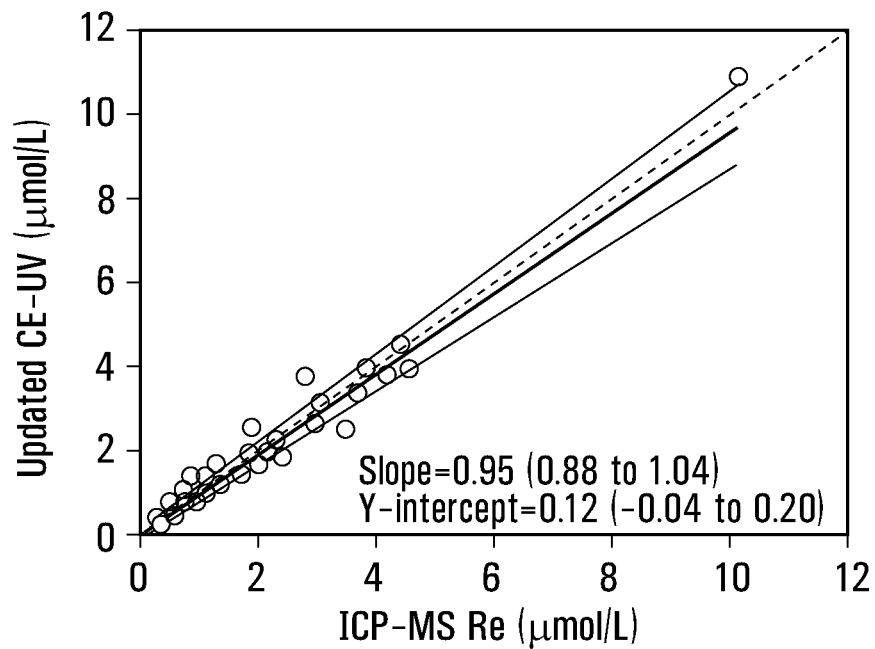
FIGS. 12A and 12B show Passing-Bablok regressions comparing the exemplary CE-UV assay when using 46 mM α-CD reported in Example 2 relative to ICP-MS using the internal standards $^{187}$Re and $^{130}$Te, respectively.
Figure 12B:
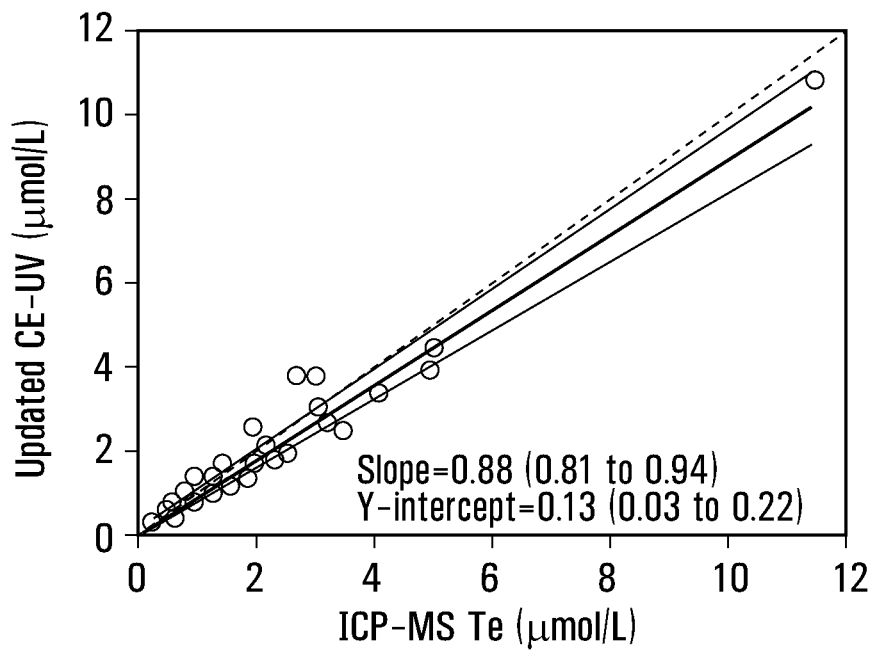
Figure 12C:
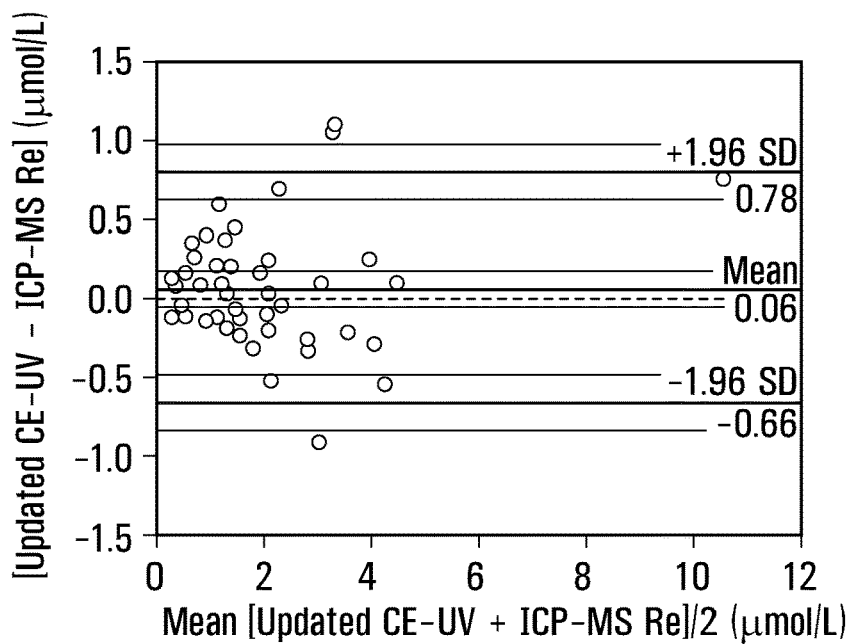
FIGS. 12C and 12E show Bland-Altman plots of differences between the exemplary CE-UV assay reported in Example 2 and ICP-MS using the internal standards $^{187}$Re and $^{130}$Te, respectively.
Figure 12D:
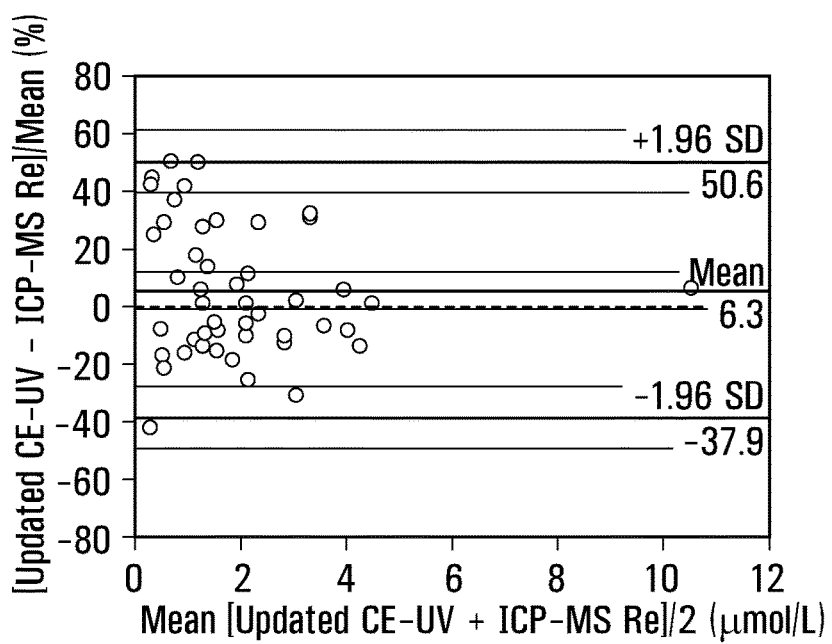
FIGS. 12D and 12F show Bland-Altman plots of percentage differences between the exemplary CE-UV assay reported in Example 2 and ICP-MS using the internal standards $^{187}$Re and $^{130}$Te, respectively. The Bland-Altman plots demonstrate good agreement between the two different methods used for urinary iodine determination.
Figure 12E:
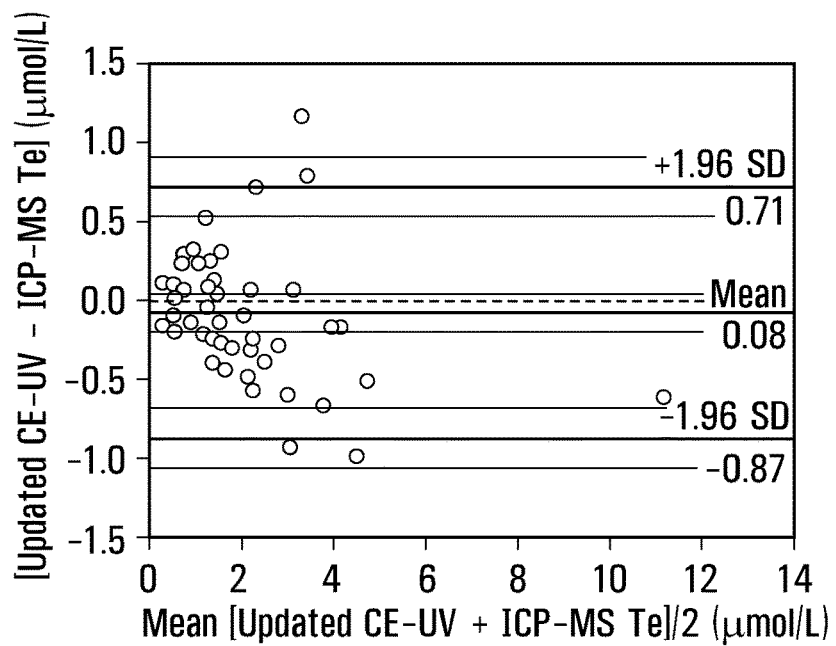
Figure 12F:
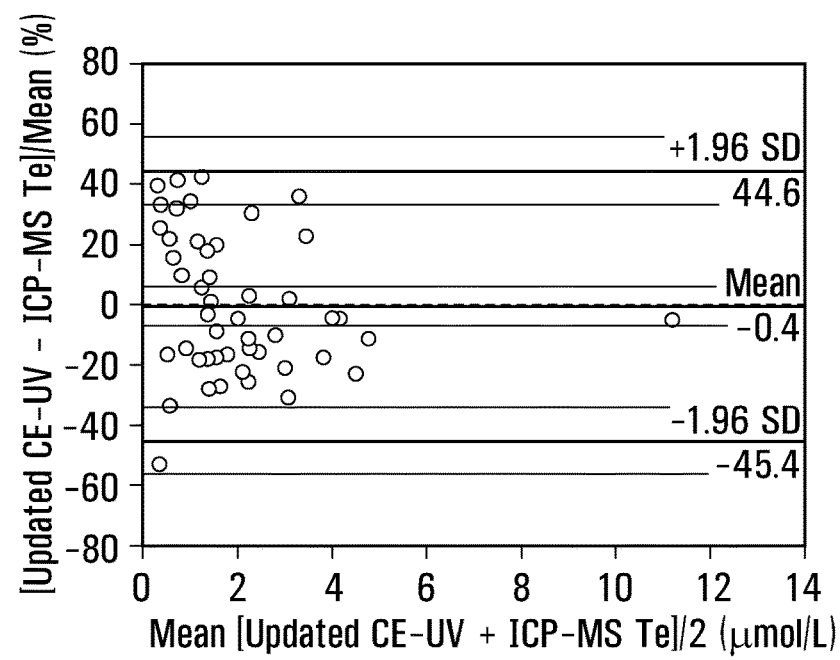

Sulfamic acid, used as a preservative for mercury analysis by ICP-MS, was also found to migrate closely to iodide, interfering with the analysis. As an exogenous oxidizing agent, sulfamic acid should be avoided in urine samples intended for iodide quantification. FIG. 11 demonstrates that the new BGE conditions (46 mM $\alpha$-CD) results in a significant recovery of iodide signal in urine samples that is independent of sulfate concentration. Table 4 also demonstrates that the modification to the BGE conditions in the CE-UV assay results in improved accuracy (<3% bias) for reliable iodide quantification in human urine samples at four different concentration levels with accuracy performance similar to results obtained from ICP-MS using two different internal standards, whereas the original CE-UV method as used in Example 1 suffers from a significant positive bias of about 40%.

TABLE 4

Mean recoveries for three independent pooled 24 h urine samples (n = 20) spiked with 0.79-3.15 µM iodide and analyzed by CE-UV and ICP-MS using two different internal standards.

| Iodide spiked | Mean recovery ± SD (%) | | | |
|---|---|---|---|---|
| (µM) | Original CE-UV | New CE-UV | ICP-MS (Re) | ICP-MS (Te) |
| 0.79 | 136.9 ± 36.0 | 100.0 ± 4.8 | 100.6 ± 2.8 | 110.8 ± 11.1 |
| 1.58 | 136.2 ± 15.0 | 99.5 ± 5.9 | 100.5 ± 3.4 | 115.0 ± 2.1 |
| 2.36 | 139.1 ± 8.6 | 102.5 ± 6.7 | 103.0 ± 1.2 | 104.5 ± 10.4 |
| 3.15 | 135.7 ± 9.8 | 102.7 ± 9.5 | 101.5 ± 0.9[a] | 113.3 ± 0.3[a] |

[a]An outlier was excluded from this calculation for ICP-MS.

FIG. 12 summarizes an inter-laboratory validation study between the updated CE-UV method and ICP-MS based on Passing-Bablok correlation and Bland-Altman difference plots, which further supports the mutual agreement of results generated between the two methods. Passing-Bablok plots show slopes and y-intercepts followed by their 95% CI. The regression, 95% CI and equality line are represented by solid, dotted and dashed lines, respectively. In the Bland-Altman plots, the mean difference/percentage difference and limits of agreement (±1.96 SD) are represented as solid lines, while their 95% CI and the zero are indicated by dotted and dashed lines, respectively.

The new CE-UV assay had excellent accuracy with far better agreement with ICP-MS results, demonstrating that the bias observed in the original method was resolved by the BGE modification involving an increase of $\alpha$-CD from 36 to 46 mM. Differences between the methods (mean, 95% CI=0.06, −0.66 to 0.79 µM for the updated CE-UV vs. ICP-MS with $^{187}$Re) are comparable with differences previously reported for a comparison between ICP-MS and the S-K assay (mean, 95% CI=0.03, −0.55 to 0.49 µmol/L).[40] Concentration-dependent differences between the methods were reported for ICP-MS vs. S-K assay, which is also consistent with our results for ICP-MS vs. the updated CE-UV method. Although ICP-MS has better precision and lower limit of quantification than the updated CE-UV assay, the method of the present application presents acceptable precision (RSD 12%) and adequate sensitivity to measure iodide levels associated to moderate deficiency (0.16-0.38 µM) according to the World Health Organization categories.

In summary, the modified BGE conditions of the CE-UV assay also constitutes a simple, robust and cost-effective method that offers excellent accuracy and robustness with adequate sensitivity for urinary iodine nutritional status determination with minimal sample pretreatment. This method is recommended as an alternative method for population-based iodine assessment in certain regions where ICP-MS is not a viable option due to its high infrastructure costs, as well as considerable operating costs related to high volume argon consumption for sample atomization.

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE APPLICATION (1) FAO; WHO. In *FAO/WHO expert consultation on human vitamin and mineral requirements*; Rome, 2001; pp. 181-194.
(2) Cavalieri, R. R. *Thyroid* 1997, 7, 177-181.
(3) WHO. *Assessment of iodine deficiency disorders and monitoring their elimination: a guide for programme managers;* 3rd ed.; WHO: Geneva, 2007.
(4) Gnat, D.; Dunn, A. D.; Chaker, S.; Delange, F.; Vertongen, F.; Dunn, J. T. *Clin. Chem.* 2003, 49, 186-188.
(5) Perrine, C. G.; Herrick, K.; Serdula, M. K.; Sullivan, K. M. *J. Nutr.* 2010, 140, 1489-1494.
(6) Andersson, M.; Karumbunathan, V.; Zimmermann, M. B. *J. Nutr.* 2012, 142, 744-750.
(7) Benoist, B.; McLean, E.; Andersson, M.; Rogers, L. *Food Nutr. Bull.* 2008, 29, 195-202.
(8) Dunn, J. T. *J. Clin. Endocrinol. Metab.* 1998, 83, 3398-3400.

(9) Trumpff, C.; De Schepper, J.; Tafforeau, J.; Van Oyen, H.; Vanderfaeillie, J.; Vandevijvere, S. *J. Trace Elem. Med. Biol.* 2013, 27, 174-183.

(10) Zimmermann, M. B. *Proc. Nutr. Soc.* 2010, 69, 133-143.

(11) Ozpinar, A.; Kelestimur, F.; Songur, Y.; Can, O.; Valentin, L.; Caldwell, K.; Arikan, E.; Unsal, I.; Serteser, M.; Inal, T.; Erdemgil, Y.; Coskun, A.; Bakirci, N.; Sezgin, O.; Blount, B. *PLoS One* 2014, 9, e88206.

(12) Zimmermann, M. B. *J. Trace Elem. Med. Biol.* 2008, 22, 81-92.

(13) Andersson, M.; de Benoist, B.; Rogers, L. Best Pract. *Res. Clin. Endocrinol. Metab.* 2010, 24, 1-11.

(14) Dunn, J. T. *J. Clin. Endocrinol. Metab.* 1996, 81, 1332-1335.

(15) Brauer, V. F. H.; Paschke, R. In *Comprehensive handbook of iodine:nutritional, biochemical, pathological, and therapeutic aspects;* Preedy, V. R.; Burrow, G. N.; Watson, R. R., Eds.; Elsevier: Amsterdam, Boston, 2009; pp. 411-420.

(16) Soldin, O. P. *Clin. Biochem.* 2002, 35, 575-579.

(17) Shelor, C. P.; Dasgupta, P. K. *Anal. Chim. Acta* 2011, 702, 16-36.

(18) Moreda-Piñeiro, A.; Romarís-Hortas, V.; Bermejo-Barrera, P. *J. Anal. At. Spectrom.* 2011, 26, 2107-2152.

(19) Romarís-Hortas, V.; Bermejo-Barrera, P.; Moreda-Piñeiro, A. *J. Chromatogr. A* 2012, 1236, 164-176.

(20) Hirokawa, T.; Yoshioka, M.; Okamoto, H.; Timerbaev, A. R.; Blaschke, G. *J. Chromatogr. B* 2004, 811, 165-170.

(21) Pantůčková, P.; Krivánková, L. *Electrophoresis* 2004, 25, 1102-1110.

(22) Huang, Z.; Ito, K.; Timerbaev, A. R.; Hirokawa, T. *Anal. Bioanal. Chem.* 2004, 378, 1836-1841.

(23) Xu, Z.; Doi, T.; Timerbaev, A. R.; Hirokawa, T. *Talanta* 2008, 77, 278-281.

(24) Hirokawa, T.; Ichihara, T.; Ito, K.; Timerbaev, A. R. *Electrophoresis* 2003, 24, 2328-2334.

(25) Timerbaev, A. R.; Fukushi, K.; Miyado, T.; Ishio, N.; Saito, K.; Motomizu, S. *J. Chromatogr. A* 2000, 888, 309-319.

(26) Macedo, A. N.; Jiwa, M. I. Y.; Macri, J.; Belostotsky, V.; Hill, S.; Britz-McKibbin, P. *Anal. Chem.* 2013, 85, 11112-11120.

(27) Gebauer, P.; Krivánková, L.; Pantůčková, P.; Bocek, P.; Thormann, W. *Electrophoresis* 2000, 21, 2797-2808.

(28) Masár, M.; Bodor, R.; Kaniansky, D. *J. Chromatogr. A* 1999, 834, 179-188.

(29) Gelb, R. I.; Schwartz, L. M.; Radeos, M.; Laufer, D. A. *J. Phys. Chem.* 1983, 87, 3349-3354.

(30) Statistics Canada. *Canadian Health Measures Survey: cycle 2 data tables-2009 to 2011;* Statistics Canada: Ottawa, 2012.

(31) Bruce, G. M.; Corey, L. M.; Mandel, J. H.; Pleus, R. C. *J. Occup. Environ. Med.* 2013, 55, 52-58.

(32) Caldwell, K L; Maxwell, C B; Makhmudov, A; Pino, S; Braverman, L E; Jones, R L; Hollowell, J G. *Clin. Chem.* 2003, 49, 1019-21.

(33) Hussain, H.; Khalid, N. M.; Selamat, R.; Wan Nazaimoon, W M. *Ann. Lab. Med.* 2013, 33: 319-325.

(34) Teo, K.; Chow, C. K.; Vaz, M.; Rangarajan, S.; Yusuf, S. *Am. Heart J.* 2009, 158, 1-7.

(35) Mervish, N.; Blount, B.; Valentin-Blasini, L.; Brenner, B.; Galvez, M. P.; Wolff, M. S.; Teitelbaum, S. L. *J. Expo. Sci. Environ. Epidemiol.* 2011, 22, 212-218.

(36) Smyth, P. P. A.; Duntas, L. H. *Horm. Metab. Res.* 2005, 353, 1-4.

(37) Caldwell, K.; Maxwell, C. B.; Makhmudov, A.; Pino, S.; Braverman, L. E.; Jones, R. L.; Hollowell, J. G. *Clin. Chem.* 2003, 49, 1019-1021.

(38) Ohashi, T.; Yamaki, M.; Pandav, C. S.; Karmarkar, M. G.; Irie, M. *Clin. Chem.* 2000, 46, 529-536.

(39) Gebauer, P.; Krivankova, L.; Pantuckova, P.; Bocek, P.; Thormann, W. *Electrophoresis* 2000, 21, 2797-2808.

(40) Caldwell, K.; Maxwell, C. B.; Makhmudov, A.; Pino, S.; Braveman, L. E.; Jones, R. L.; Hollowell, J. G. *Clin. Chem.* 2003, 49, 1019-1021.

The invention claimed is:

1. A method for determining iodide content in a sample comprising:
   a) subjecting the sample to sample self-stacking via transient isotachophoresis followed by zonal electrophoresis in which a background electrolyte (BGE) comprising a hydroxide salt, a complexing agent and an inorganic acid is used to generate an electropherogram; and
   b) determining the content of iodide in the sample from the electropherogram,
   wherein the BGE has a pH in the range of about 2 to about 4.

2. The method of claim 1, wherein the zonal electrophoresis is capillary electrophoresis (CE).

3. The method of claim 1, wherein the sample is diluted with deionized water by about 1.5-fold to about 4-fold.

4. The method of claim 1, wherein an internal standard is added to the sample.

5. The method of claim 1, wherein the sample is selected from bodily fluids, and environmental, food and drink samples.

6. The method of claim 4, wherein the sample is a human bodily fluid.

7. The method of claim 6, wherein the human bodily fluid is selected from urine, sweat and blood.

8. The method of claim 1, wherein the hydroxide salt is present in the BGE in an amount of from about 150 mM to about 200 mM.

9. The method of claim 8, wherein the hydroxide salt is lithium hydroxide.

10. The method of claim 1, wherein the complexing agent is present in the BGE in an amount of from about 30 mM to about 60 mM.

11. The method of claim 10, wherein the complexing agent is α-cyclodextrin.

12. The method of claim 1, wherein the inorganic acid is present in the BGE in an amount of from about 150 mM to about 200 mM.

13. The method of claim 12, wherein the inorganic acid is phosphoric acid.

14. The method of claim 1 further comprising determining one or more iodide uptake inhibitor content in the sample wherein, the content of the one or more iodide uptake inhibitors in the sample is also determined from the electropherogram.

15. The method of claim 14, wherein the one or more iodide uptake inhibitors are selected from nitrate, bromide and thiocyanate.

16. A method for monitoring iodine deficiency in a population by determining iodide content in a sample from a representative number of subjects from the population using the method of claim 1.

17. The method of claim 16, wherein the subject has an iodine deficiency disorder.

18. The method of claim 17, wherein the iodine deficiency disorder is selected from impaired cognitive development in children, weight gain, depression, thyroid-related disorders, cancer and cardiovascular diseases.

19. A method for monitoring iodine deficiency in a population by determining iodide content and one or more iodide inhibitor content in a sample from a representative number of subjects from the population using the method of claim 14.

20. The method of claim 1, wherein the BGE has a pH of about 3.

* * * * *